(12) United States Patent
Tuller et al.

(10) Patent No.: US 11,610,650 B2
(45) Date of Patent: Mar. 21, 2023

(54) METHOD AND SYSTEM FOR DESIGNING POLYNUCLEOTIDE SEQUENCES AND POLYNUCLEOTIDE SEQUENCES OBTAINED THEREBY

(71) Applicant: Ramot at Tel-Aviv University Ltd., Tel-Aviv (IL)

(72) Inventors: Tamir Tuller, Herzeliya Pituach (IL); Hadas Zur, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/723,875

(22) Filed: May 28, 2015

(65) Prior Publication Data

US 2015/0347677 A1    Dec. 3, 2015

Related U.S. Application Data

(60) Provisional application No. 62/004,273, filed on May 29, 2014.

(51) Int. Cl.

| | |
|---|---|
| *C12N 15/79* | (2006.01) |
| *G16B 30/00* | (2019.01) |
| *G16B 35/00* | (2019.01) |
| *G16C 20/60* | (2019.01) |
| *C12N 15/10* | (2006.01) |
| *G06F 17/00* | (2019.01) |
| *G06F 17/10* | (2006.01) |
| *G06F 17/15* | (2006.01) |
| *G06F 17/17* | (2006.01) |

(52) U.S. Cl.
CPC ......... *G16B 30/00* (2019.02); *C12N 15/1089* (2013.01); *G06F 17/00* (2013.01); *G06F 17/10* (2013.01); *G06F 17/15* (2013.01); *G06F 17/17* (2013.01); *G16B 35/00* (2019.02); *G16C 20/60* (2019.02)

(58) Field of Classification Search
CPC .... C12N 25/67; C12N 15/1089; C40B 30/02; G06F 19/10; G06F 19/12; G06F 19/22
See application file for complete search history.

(56) References Cited

U.S. PATENT DOCUMENTS

| | | | | |
|---|---|---|---|---|
| 7,158,889 B2* | 1/2007 | Hussan | .......... | G06F 19/22 435/4 |
| 8,224,578 B2* | 7/2012 | Raab | .......... | C07K 14/535 702/19 |
| 2009/0208955 A1* | 8/2009 | Robins | .......... | G06F 19/22 435/6.11 |
| 2014/0244228 A1* | 8/2014 | Lee | .......... | G06F 19/22 703/11 |
| 2014/0371109 A1* | 12/2014 | McMillen | .......... | G06F 13/4068 702/20 |

FOREIGN PATENT DOCUMENTS

| | | |
|---|---|---|
| WO | WO 2011/111034 | 9/2011 |

OTHER PUBLICATIONS

Condon et al., Efficient codon optimization with motif engineering. Journal of Discrete Algorithms. vol. 16, Oct. 2012, pp. 104-112.*
Ding et al., CodingMotif: exact determination of over represented nucleotide motifs in coding sequences. Bioinformatics 2012, 13:1-16.*
Moura et al. Codon-triplet context unveils unique features of the Candida albicans protein coding genome. BMC Genomics 2007, 8: 444. 1-14 (Year: 2007).*
Rajic et al., Size of the protein-coding genome and rate of molecular evolution. J Hum Genet (2005) 50:217-229 (Year: 2005).*
Manber et al. "Suffix Arrays: A New Method for On-Line String Searches", Proceedings of the First Annual ACM-SIAM Symposium on Discrete Algorithms, p. 319-327, 1990.
Dos Reis et al. "Solving the Riddle of Codon Usage Preferences: A Test for Translational Selection", Nucleic Acids Research, 32(17): 5036-5044, Sep. 24, 2004.
Goodman el al. "Causes and Effects of N-Terminal Codon Bias in Bacterial Genes", Science, 342(6157): 474-479, Epub Sep. 26, 2013.
Gustafsson et al. "Codon Bias and Heterologous Protein Expression", Trends in Biotechnology, 22(7): 346-353, Jul. 2004.
Kudla et al. "Coding-Sequence Determinants of Gene Expression in *Escherichia Coli*", Science, 324(5924): 255-258, Apr. 10, 2009.
Sharp et al. "The Codon Adaptation Index—A Measure of Directional Synonymous Codon Usage Bias, and Its Potential Applications", Nucleic Acids Research, 15(3): 1281-1295, Feb. 11, 1987.
Vervoort et al. "Optimizing Heterologous Expression in Dictyostelium: Importance of 5' Codon Adaptation", Nucleic Acids Research, 28(10): 2069-2074, May 15, 2000.

* cited by examiner

*Primary Examiner* — Arthur S Leonard

(57) ABSTRACT

Methods of designing a polynucleotide sequence for expressing a polypeptide-of-interest in a cell are provided. Also provided are artificial transcript sequences generated according to the present teachings. Further provided are methods of estimating the adaptiveness of a transcript sequence encoding a polypeptide-of-interest to a gene expression machinery in a cell.

21 Claims, 10 Drawing Sheets
(8 of 10 Drawing Sheet(s) Filed in Color)

FIG. 5A
FIG. 5B
FIG. 5C
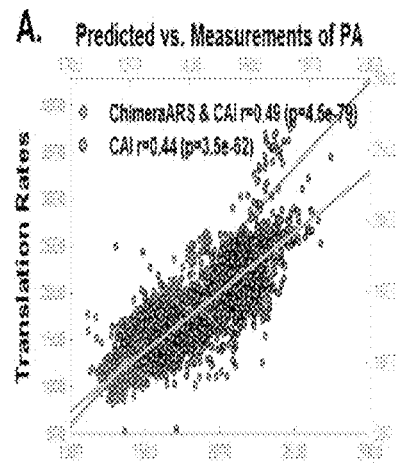
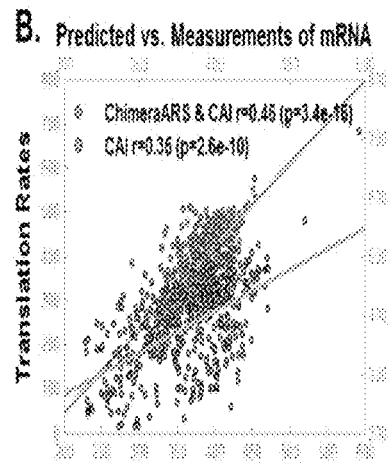
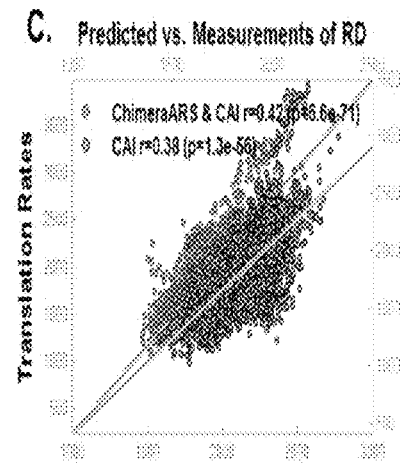
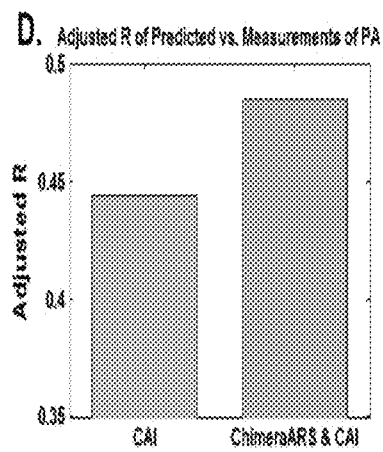
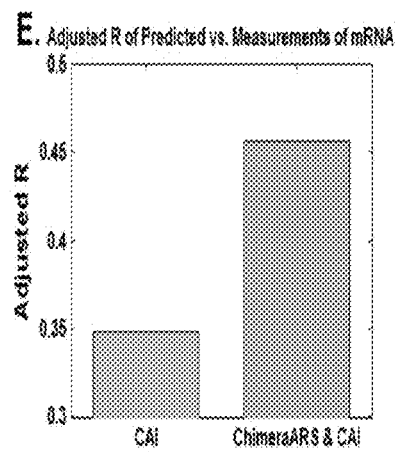
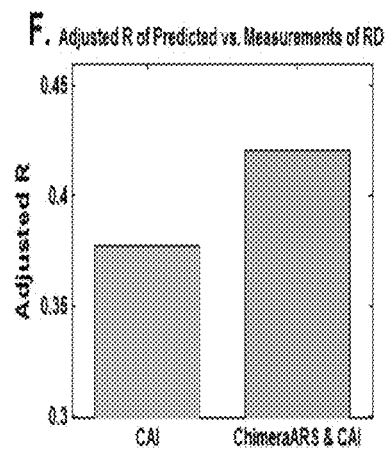
FIG. 5D
FIG. 5E
FIG. 5F FIG. 6A
FIG. 6B
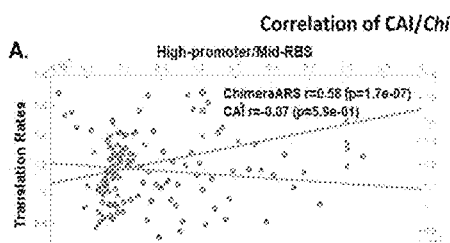
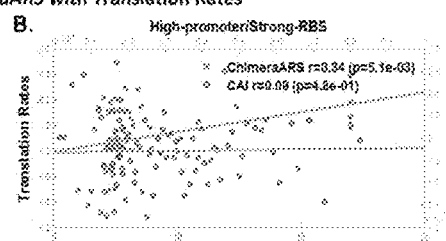
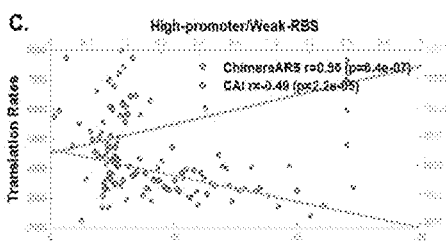
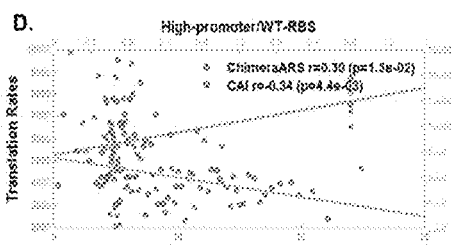
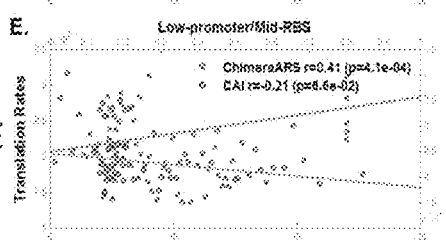
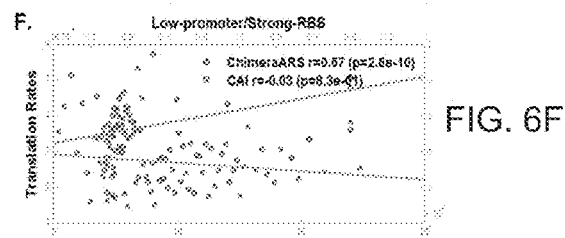
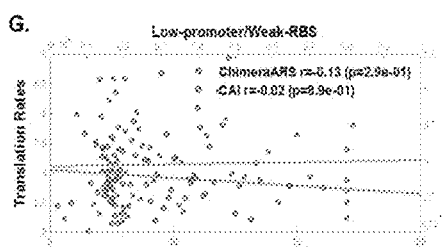
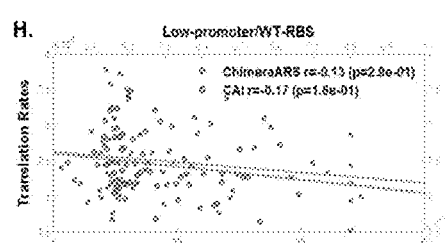
FIG.6C
FIG. 6D
FIG. 6E
FIG. 6F
FIG. 6G
FIG. 6H

```
         ┌─────────────┐
         │     10      │
         │   begin     │
         └──────┬──────┘
                │
  ┌─────────────┴──────────────────────────────────────────────┐
  │                            11                               │
  │ input: a sequence describing the polypeptide a reference    │
  │              set of sequences and                           │
  └─────────────┬──────────────────────────────────────────────┘
                │
  ┌─────────────┴──────────────────────────────────────────────┐
  │                            12                               │
  │   identify sufficiently long and/or frequent strings in     │
  │                    the reference set                        │
  └─────────────┬──────────────────────────────────────────────┘
                │
  ┌─────────────┴──────────────────────────────────────────────┐
  │                            13                               │
  │       embed the identified string in a transcript sequence  │
  └─────────────┬──────────────────────────────────────────────┘
                │
         ┌──────┴──────┐
         │     14      │
         │    end      │
         └─────────────┘
```

FIG. 7

```
         ┌─────────────┐
         │     20      │
         │   begin     │
         └──────┬──────┘
                │
  ┌─────────────┴──────────────────────────────────────────────┐
  │                            21                               │
  │ input: a sequence describing the polypeptide and a          │
  │            reference set of sequences                       │
  └─────────────┬──────────────────────────────────────────────┘
                │
  ┌─────────────┴──────────────────────────────────────────────┐
  │                            22                               │
  │    generate a list of strings for each position along       │
  │                     the sequence                            │
  └─────────────┬──────────────────────────────────────────────┘
                │
  ┌─────────────┴──────────────────────────────────────────────┐
  │                            23                               │
  │  process the list of strings based on the length and/or     │
  │              frequency of the string                        │
  └─────────────┬──────────────────────────────────────────────┘
                │
  ┌─────────────┴──────────────────────────────────────────────┐
  │                            24                               │
  │     calculate a statistical measure for the processed list  │
  └─────────────┬──────────────────────────────────────────────┘
                │
         ┌──────┴──────┐
         │     25      │
         │    end      │
         └─────────────┘
```

FIG. 8

METHOD AND SYSTEM FOR DESIGNING POLYNUCLEOTIDE SEQUENCES AND POLYNUCLEOTIDE SEQUENCES OBTAINED THEREBY

RELATED APPLICATION

This application claims the benefit of priority under 35 USC 119(e) of U.S. Provisional Patent Application No. 62/004,273 filed May 29, 2014, the contents of which are incorporated herein by reference in their entirety.

FIELD AND BACKGROUND OF THE INVENTION

The present invention, in some embodiments thereof, relates to bioinformatics and, more particularly, but not exclusively, to methods of designing polynucleotide sequences for heterologous or endogenous expression and polynucleotide sequences obtained thereby.

The inherent redundancy of the genetic code, where 61 codons encode only 20 amino acids, is a widely studied phenomenon [1-3]. In recent years it has been shown that various gene expression regulatory aspects are interleaved in this redundancy. Specifically, during its lifetime the mRNA sequence interacts with various intracellular molecules and complexes such as the spliceosome [4], pre-initiation complex [5, 6], ribosomes [7] and ribosomal RNA composing it [8], tRNAs [9], miRNAs [10], other mRNAs [11], proteins [12] (including transcription factors [13]), and the mRNA sequence itself via its folding [14, 15] (see FIG. 1). The affinity of these interactions is affected by the nucleotide composition in various parts of the transcript (see for example [1, 2, 5, 6, 8-14, 16-19]), and can usually be described by Markovian models and/or position specific scoring matrices (PSSMs) [20]. However, there are debates regarding the nature and the efficiency of some of these interactions (see for example [1]).

Several studies have been directed at investigating coding-sequence determinants of gene expression. In [17], for example, a synthetic library of 154 genes that varied randomly at synonymous sites, but all encoded the same green fluorescent protein (GFP), has been engendered. In [23], expression from synthetic reporters in *Escherichia coli* was measured, and it was found that N-terminal rare codons significantly increase expression.

Additional background art includes: [25], [26] and WO2011/111034.

SUMMARY OF THE INVENTION

According to some embodiments of the invention there is provided a method of designing a polynucleotide sequence for expressing a polypeptide-of-interest (POI) in a host cell. The method comprises identifying in a reference set of polynucleotide sequences of the host cell at least one string of genetic elements, wherein each of the at least one string is at least 4 nucleotides long and is capable of encoding a portion of the POI, and embedding the at least one string in a transcript sequence encoding the POI.

According to an aspect of some embodiments of the present invention there is provided a method of designing a polynucleotide sequence for increasing expression of a POI in a cell, wherein the polypeptide of interest is endogenous to the cell. The method comprises identifying in a reference set of polynucleotide sequences of the cell at least one string of genetic elements, wherein each of the at least one string is at least 4 nucleotides long and is capable of encoding a portion of the POI, wherein the at least one string is not of a polynucleotide natively encoding the POI, and embedding the at least one string in a transcript sequence encoding the POI.

According to some embodiments of the invention the identification comprises identifying a plurality of strings of genetic elements.

According to some embodiments of the invention the method comprises processing the plurality of strings by a dynamic programming method.

According to some embodiments of the invention the processing comprises minimizing or reducing a number of the plurality of strings.

According to some embodiments of the invention the identifying is according to a frequency of occurrence of the string in the reference set.

According to some embodiments of the invention the method comprises searching for a subsequence having a maximal length among subsequences that are common to the POI and the reference set of polynucleotide sequences, wherein the identifying is based in part on the maximal length.

According to some embodiments of the invention the method comprises processing the plurality of strings by a dynamic programming method. Optionally, but not necessarily, the dynamic programming method is characterized by a recursion depth which is at most the maximal length.

According to some embodiments of the invention the identifying and embedding is effected computationally.

According to some embodiments of the invention the string(s) is identified by analyzing in each codon or nucleotide position in the transcript sequence a longest string of nucleotides that starts in the position and is present in the reference set of polynucleotide sequences.

According to an aspect of some embodiments of the present invention there is provided a method of estimating the adaptiveness of a transcript sequence encoding a POI to a gene expression machinery in a host cell. The method comprises for each of a plurality of positions along the transcript sequence, generating a list of strings of genetic elements, each string being a subsequence of the transcript sequence, and is also a subsequence of at least one sequence of a reference set of polynucleotide sequences of the host cell. The method further comprises processing each of at least a few of the lists to select a string of genetic elements based on a length of the string, thereby providing a processed list of strings of genetic elements; and calculating at least one statistical measure for the processed list, wherein the at least one statistical measure is indicative of the adaptiveness of the transcript sequence to the gene expression machinery.

According to an aspect of some embodiments of the present invention there is provided a method of estimating the adaptiveness of a transcript sequence encoding a POI to a gene expression machinery in a cell, wherein the transcript sequence is endogenous to the cell. The method comprises for each of a plurality of positions along the transcript sequence, generating a list of strings of genetic elements, each string being a subsequence of the transcript sequence, and is also a subsequence of at least one sequence of a reference set of polynucleotide sequences of the host cell. The method further comprises processing each of at least a few of the lists to select a string of genetic elements based on a length of the string, thereby providing a processed list of strings of genetic elements; and calculating at least one statistical measure for the processed list, wherein the at least one statistical measure is indicative of the adaptiveness of the transcript sequence to the gene expression machinery.

According to some embodiments of the invention the string is selected based only on the length.

According to some embodiments of the invention the selected string has a length above a length threshold.

According to some embodiments of the invention the length threshold is a predetermined fixed threshold.

According to some embodiments of the invention the length threshold is dynamically updated during the processing.

According to some embodiments of the invention the selected string is a longest string in the list.

According to some embodiments of the invention the statistical measure is based on a sum of lengths of the selected strings in the processed list.

According to some embodiments of the invention the statistical measure comprises at least one measure selected from the group consisting of mean length, median length supremum length and infimum length, any combination thereof and any function thereof.

According to some embodiments of the invention the length is calculated in terms of amino acids.

According to some embodiments of the invention the length is calculated in terms of codons.

According to some embodiments of the invention the length is calculated in terms of nucleotides.

According to some embodiments of the invention the method comprises generating the reference set of polynucleotide sequences.

According to an aspect of some embodiments of the present invention there is provided an artificial transcript having a nucleic acid sequence encoding a POI designed for expression in a host cell, the host cell being characterized by a reference set of polynucleotide sequences, the artificial transcript comprising at least one string of genetic elements being at least 4 nucleotides in length, the at least one string being embedded in the nucleic acid sequence to as to encode the POI, the at least one string being represented in the reference set of polynucleotide sequences, and wherein the at least one string and the nucleic acid sequence are heterologous and with the proviso that when the at least one string is a single string of genetic elements, the single string is not located at a 5' terminus of the nucleic acid sequence.

According to some embodiments of the invention the host cell is heterologous to the POI.

According to some embodiments of the invention the host cell endogenously expresses the POI.

According to an aspect of some embodiments of the present invention there is provided an artificial transcript obtainable according to the method as delineated above and optionally and preferably as further detailed hereinbelow.

According to some embodiments of the invention the at least one string comprises at least two strings.

According to some embodiments of the invention the at least two strings are separated by a gap.

According to some embodiments of the invention the string(s) comprise a coding sequence.

According to some embodiments of the invention the string(s) comprise a non-coding sequence.

According to some embodiments of the invention the genetic elements are codon fragments.

According to some embodiments of the invention the genetic elements are codon pairs.

According to some embodiments of the invention the genetic elements are nucleotides.

According to some embodiments of the invention the reference set of polynucleotide sequences is selected from the group consisting of genomic DNA, RNA and ESTs.

According to some embodiments of the invention the ESTs are cell-specific or tissue specific.

According to some embodiments of the invention the reference set of polynucleotide sequences is normalized.

According to some embodiments of the invention the POI is selected from the group consisting of an antibody, insulin, interferon, growth hormone, erythropoietin, growth hormone, follicle stimulating hormone, factor VIII, low density lipoprotein receptor (LDLR) alpha galactosidase A and glucocerebrosidase.

According to some embodiments of the invention the host cell is a Eukaryotic, Prokaryotic or Archaeal cell.

According to some embodiments of the invention the host cell is of a species selected from the group consisting of a bacterial species, a yeast species, a fungal species, an algal, a plant species, an insect species and a mammalian species.

According to some embodiments of the invention the bacterial species comprise *E. coli* cells.

According to some embodiments of the invention the cells of a mammalian species comprise Chinese hamster ovary (CHO) cells.

According to some embodiments of the invention the cells of the yeast species comprise *S. cerevisiae* cells.

According to some embodiments of the invention the cells comprise algal cells.

According to an aspect of some embodiments of the present invention there is provided an expression construct comprising the polynucleotide expressing the artificial transcript as delineated above and optionally and preferably as further detailed below and a promoter suitable for expressing the artificial transcript in the host cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically (preferably computationally), or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of macro-molecules that interact with a transcript and specifically the open reading frame (ORF), and the regulatory signals interleaved in a genetic code;

FIG. 2A is a schematic illustration of a procedure for calculating a score, referred to herein as a ChimeraARS score, that describes the adaptiveness of a transcript sequence encoding a polypeptide-of-interest (POI) to a gene expression machinery in a host cell, according to some embodiments of the present invention;

FIG. 2B is a schematic illustration of procedure, referred to herein as the ChimeraMap procedure, suitable for designing a polynucleotide sequence for expressing or increasing expression of a POI in a cell, according to some embodiments of the present invention;

FIG. 3A shows ChimeraARS scores of genes designed by the ChimeraMap procedure, as compared to averaged 100 randomizations, of the *E. coli* subset of genes, obtained by performing experiments according to some embodiments of the present invention;

FIG. 3B shows ChimeraARS scores of genes designed by the ChimeraMap procedure, as compared to CAI (codon adaptation index) rationale scores of the *E. coli* subset modified by replacing synonymous codons with their most abundant version, obtained by performing experiments according to some embodiments of the present invention;

FIG. 4A shows ChimeraARS scores for real and randomized *E. coli* genome, as obtained by performing experiments according to some embodiments of the present invention;

FIG. 4B shows ChimeraARS scores for the *E. coli* real and random genome, as designed according to some embodiments of the present invention by the ChimeraMap procedure;

FIG. 4C shows ChimeraARS scores for the real and randomized *E. coli* genome which maintains codon pairs distribution, in addition to single codon distribution and encoded protein, as obtained by performing experiments according to some embodiments of the present invention;

Figure 9:
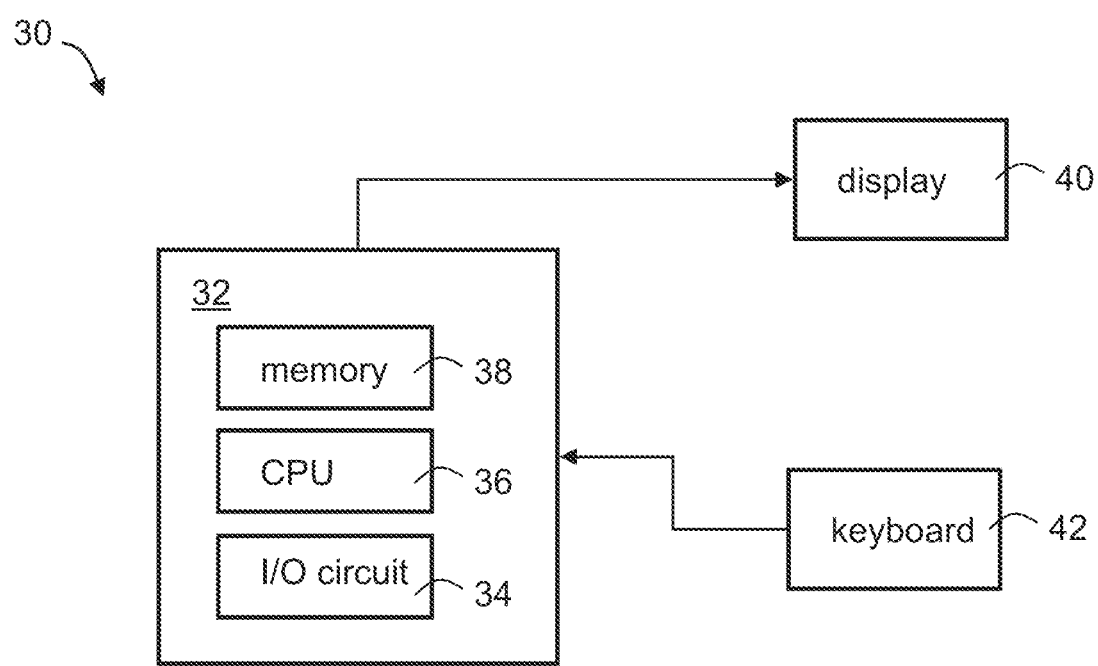
Figure 10:
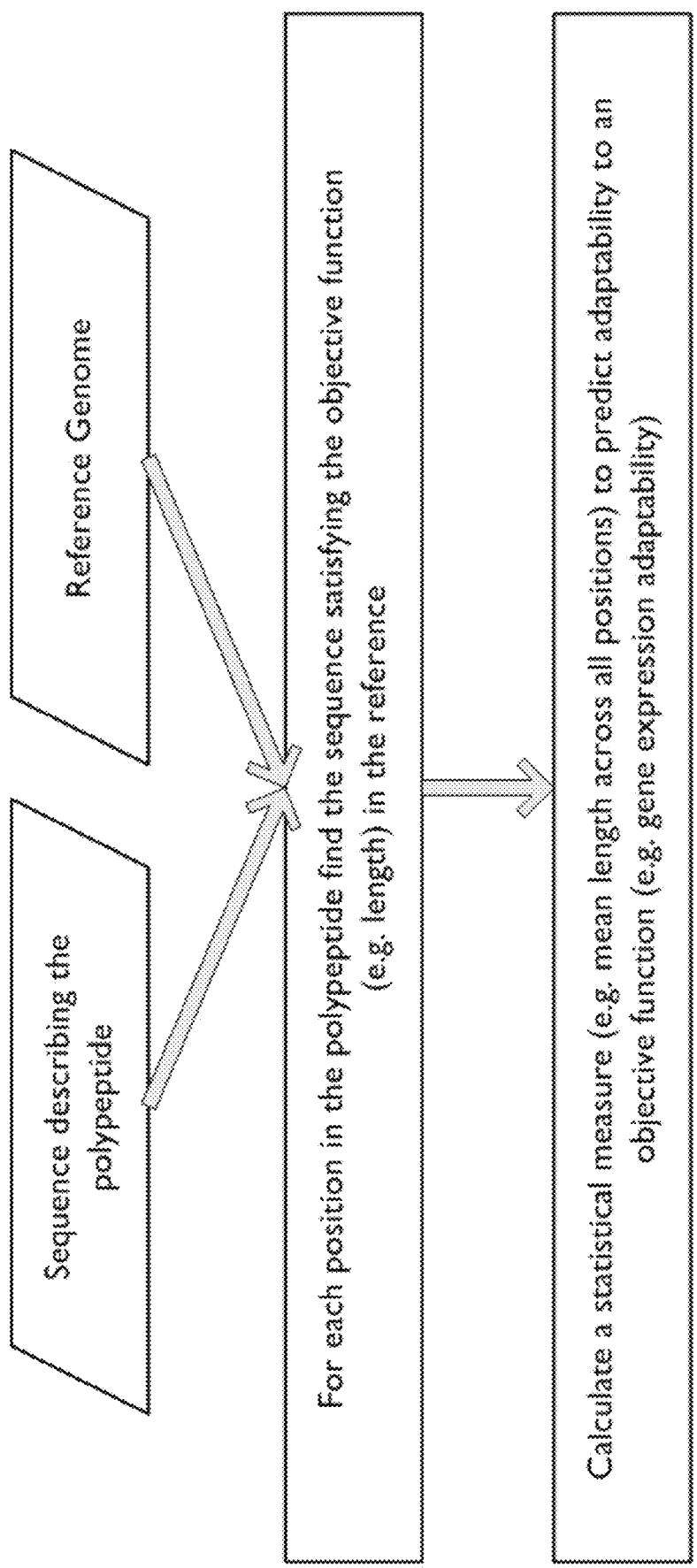
Figure 11:
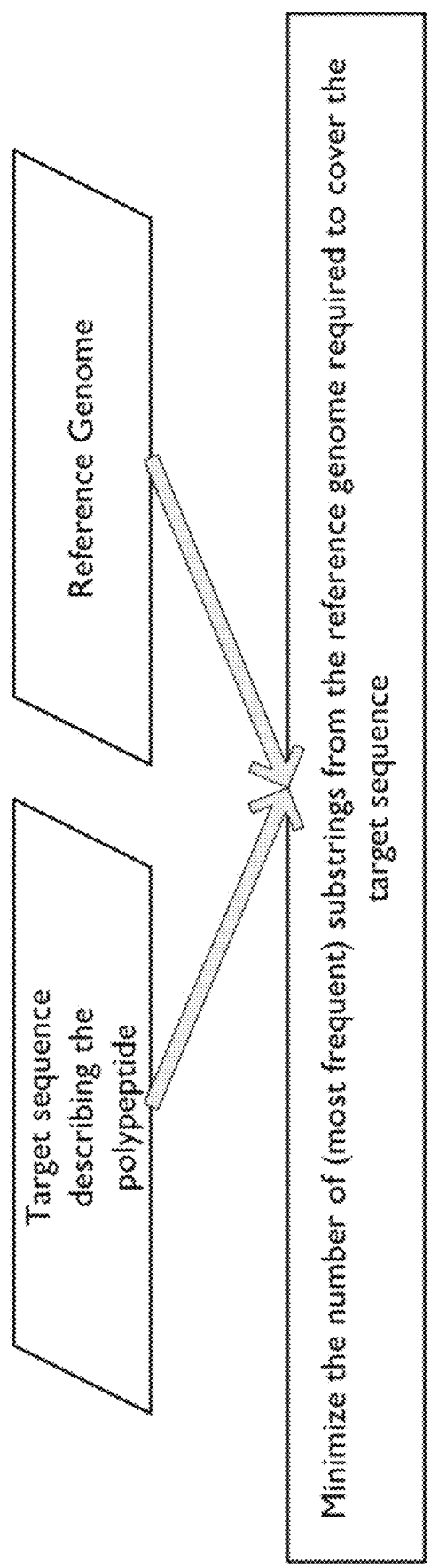

FIGS. 5A-F are dot plots (FIGS. 5A-C) and histograms of adjusted Spearman correlations (FIGS. 5D-5F) describing a regression model based only on Codon Adaptation Index (gray), and a model based on the Codon Adaptation Index and ChimeraARS (pale blue), vs. measured protein abundance (FIGS. 5A and 5D), mRNA levels (FIGS. 5B and 5E), and ribosomal density (FIGS. 5C and 5F), respectively, as obtained by performing experiments according to some embodiments of the present invention;

FIGS. 6A-H show the Spearman correlation between the ChimeraARS score obtained according to some embodiments of the present invention and the Codon Adaptation Index with *E. coli* heterologous translation rates respectively;

FIG. 7 is a flowchart diagram of a method designing a polynucleotide sequence for expressing or increasing expression of a POI in a cell, according to some embodiments of the present invention;

FIG. 8 is a flowchart diagram describing a method suitable for estimating the adaptiveness of a transcript sequence encoding a POI to the gene expression machinery in a host cell, according to some embodiments of the present invention;

FIG. 9 is a schematic illustration of a data processing system, which can be used for executing the method illustrated in FIG. 7 or the method illustrated in FIG. 8;

FIG. 10 is a flowchart diagram describing a procedure for calculating the ChimeraARS score, according to some embodiments of the present invention; and FIG. 11 is a flowchart diagram describing the ChimeraMap procedure, according to some embodiments of the present invention.

DESCRIPTION OF SPECIFIC EMBODIMENTS OF THE INVENTION

The present invention, in some embodiments thereof, relates to bioinformatics and, more particularly, but not exclusively, to methods of designing polynucleotide sequences for heterologous or endogenous expression and polynucleotide sequences obtained thereby.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Conventional methods for estimating the adaptiveness of a transcript to the gene expression regulatory machinery are based on single codon usage bias [21, 22]. It was nevertheless realized by the present inventors that these methods fail to exhibit meaningful relations with the expression levels of genes. The present inventors found that such indexes cannot fully capture all the gene expression information encoded in the ORF as some of it is not directly related to codon decoding. For example, the binding site of miRNAs is around 22nd, information not fully described by the independent distribution of single codons.

The present inventors found a technique that captures many aspects of gene expression regulation, by extracting high-dimensional statistical information from sequence data. The extracted information is "high-dimensional" in the sense that it relates to substrings of nucleotides that are typically longer than codons. While conceiving the present invention it has been hypothesized, and while reducing the present invention to practice it has been realized, that this type of statistical information encapsulates many types of intracellular interactions.

Another difficulty conventional methods face relates to the size and diversity of the available sequence data. Conventional techniques are based on gene expression measurements (mRNA levels, protein levels, ribosomal densities, etc.) for extracting information related to the biophysical nature of the interactions of macro-molecules with the ORF.

However, today there are about 26,000 genomes of different organisms, but large scale gene expression information (e.g., protein abundance measurements (PA)) is available for only a few dozen [24].

In light of the growing surge of new studies reporting novel rules related to the way aspects of gene expression are encoded in the transcript [1, 6, 8, 13], it was realized by the present inventors that many additional rules are yet to be deciphered. It was further realized by the present inventors that many of the established rules are organism specific and/or condition specific and/or tissue specific, and may not hold in different organisms and/or different conditions than those used for their inference.

While conceiving the present invention, the present inventors have devised a computational technique for optimizing gene expression. The technique is referred to below as Chimera, and can be used for exploiting hidden high dimensional information in sequence data (e.g., ORFs, introns, UTRs) of the genome of the analyzed organism.

In some embodiments, the Chimera technique is used for calculating a score that describes the adaptiveness of a genetic sequence (such as, but not limited to, coding sequence, transcript sequence, UTRs, introns, etc) to the gene expression machinery of a host cell. This score is referred to below as a Chimera Average Repetitive Substring (ChimeraARS) score.

In various exemplary embodiments of the invention the calculated score describes the tendency of the genetic sequence to include relatively long subsequences that appear in a reference set of sequences, where the reference set of sequences is indicative of the gene expression machinery (e.g., translational machinery, transcriptional machinery) of the host cell.

In some embodiments, the Chimera technique is used as a computerized procedure for designing a polynucleotide sequence for expressing a polypeptide-of-interest (POI) in a host cell. In some embodiments of the present invention the host is a heterologous host cell, and in some embodiments of the present invention the host cell is an endogenous host cell. This procedure is referred to herein as the ChimeraMap procedure. In various exemplary embodiments of the invention the procedure selects the polynucleotide sequence such that it includes relatively long genetic subsequences (e.g., relatively long subsequences of codons or relatively long subsequences of nucleotides) that appear in the coding sequences of the host cell.

Thus, both the ChimeraARS score and the ChimeraMAP procedure are optionally and preferably based on the observation made by the present inventors that relatively long and/or frequent (and optionally having other properties) subsequences are more adapted to the cellular gene expression machinery than shorter subsequences.

As used herein the term "designing" refers to bioinformatic design which may be effected computationally or experimentally. The purpose of this method is to improve expression (or to improve protein functionality, properties, or folding, etc), hence the teachings as presented herein may also be referred to as a method of codon optimization, and more generally of nucleotide (or sequence) optimization.

The phrase "codon optimization" refers to the selection of appropriate DNA nucleotides for use within a structural gene or fragment thereof that approaches codon usage within a particular organism or in particular set of genes (e.g., gene families, genes which are co-regulated, tissue/cell specific genes, developmentally regulated genes) or region within a gene. Therefore, an optimized gene or nucleic acid sequence refers to a gene in which the nucleotide sequence of a native or naturally occurring gene has been modified in order to better fit the intracellular gene expression machinery (for example, via utilizing statistically-preferred or statistically-favored codons within an organism; as well as non-coding regions). The nucleotide sequence typically is examined at the DNA or RNA level, and the coding region as well as in non-coding regions such as UTRS and introns (or any genomic fragment), optimized for expression in a particular organism determined using any suitable procedure. When optimizing non-coding fragments, to which codon usage does not apply, the optimization is based on existing/repetitive nucleotide subsequences.

As used herein the phrase "polynucleotide sequence" or "an artificial transcript" refers to a single or double stranded nucleic acid sequence which is isolated and provided in the form of an RNA sequence (i.e. comprising ribonucleotides), a complementary polynucleotide sequence (cDNA), a genomic polynucleotide sequence (i.e. comprising deoxyribonucleotides) and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As is illustrated hereinbelow and in the Examples section which follows, the present inventors have demonstrated the applicability of the new approach for analyzing and engineering heterologous genes and endogenous genes. Specifically, focusing on E. coli, the present inventors have shown that it can exploit information that cannot be detected by conventional approaches (e.g. the CAI—Codon Adaptation Index), which only consider single codon distributions; for example, the present inventors report correlations of up to 0.67 for the ChimeraARS measure with heterologous gene expression, when the CAI yielded no correlation.

Reference is now made to FIG. 7 which is a flowchart diagram of a method designing a polynucleotide sequence for expressing or increasing expression of a POI in a cell, according to some embodiments of the present invention.

Any of the methods described herein can be embodied in many forms. For example, it can be embodied in on a tangible medium such as a computer for performing the method operations. It can be embodied on a computer readable medium, comprising computer readable instructions for carrying out the method operations. It can also be embodied in an electronic device having digital computer capabilities arranged to run the computer program on the tangible medium or execute the instruction on a computer readable medium.

Computer programs implementing the method according to some embodiments of this invention can commonly be distributed to users on a distribution medium such as, but not limited to, CD-ROM, flash memory devices, flash drives, or, in some embodiments, drives accessible by means of network communication, over the internet (e.g., within a cloud environment), or over a cellular network. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. Computer programs implementing the method according to some embodiments of this invention can also be executed by one or more data processors that belong to a cloud computing environment. All these operations are well-known to those skilled in the art of computer systems. Data used and/or provided by the method of the present embodiments can be transmitted by means of network communication, over the internet, over a cellular network or over any type of network, suitable for data transmission.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method of the present embodiments can be utilized for any type of cells, including, without limitation, a cell culture, a whole organism, or a part of an organism. The method begins at 10 and optionally and preferably continues to 11 at which the method receives as input a sequence describing the POI, and a reference set of sequences. The set and sequence describing the POI can be received from a local computer-readable storage medium or over a communication network.

The sequence describing POI can be, for example, a transcript sequence, a sequence of codons, or the like. The reference set preferably includes sequences of genetic material that are characteristic to the cell. For example, the reference set can include the entire genome, or only highly expressed genes, or only tissue specific genes, or only genes with a specific function or only genes with a specific property. In some embodiments of the present invention, the method generates the reference set instead of receiving. This can be done, for example, by applying a sequencing technology to the cell (e.g., polynucleotide sequencing, whole genome sequencing, etc.).

When the method is utilized for expressing the POI in a host cell, the host is preferably a heterologous host cell. When the method is utilized for increasing the expression of the POI in a cell, the POI is preferably endogenous to the cell.

The method continues to 12 at which the method identifies in the reference set one or more sufficiently long and/or sufficiently frequent strings of genetic elements that encode a portion of the POI. The genetic elements of the identified string(s) may be selected from the group consisting of nucleotides, codons, codon pairs, and codon fragments. When the genetic elements are codon fragments, each fragment can optionally and preferably represent a codon. For example, a codon can be divided to fragments assumed to be identical or similar, wherein the genetic elements building the string can include one fragment of each divided codon.

At least one, more preferably each, of the identified strings optionally and preferably has a length which is above a predetermined threshold length. Typically, the threshold length is 2 genetic elements or 3 genetic elements or 4 genetic elements or 5 genetic elements or 6 genetic elements or 7 genetic elements or 8 genetic elements or 9 genetic elements or 10 genetic elements or 50 genetic elements or 100 genetic elements or 500 genetic elements.

Thus, according to some embodiments, the identified string comprises 2-100 or 2-1000 strings of genetic elements, according to some embodiments, the identified string is 4-1000 genetic elements in length, according to some embodiments, the identified string is 10-1000 genetic elements in length, according to some embodiments, the identified string is 4-500 genetic elements in length, according to some embodiments, the identified string is 4-100 genetic elements in length, according to some embodiments, the identified string is 4-50 genetic elements in length, according to some embodiments, the identified string is 7-30 genetic elements in length, according to some embodiments, the identified string is 10-30 genetic elements in length, according to some embodiments, the identified string is 15-30 genetic elements in length.

According to a specific embodiment, at least one of the identified strings comprises a codon fragment.

As used herein "codon fragment" refers to an incomplete codon, namely a string having less than 3 bases.

Thus, for example, a string of 4 nucleotides can comprise a complete codon (3 bases)+1 base. Alternatively, a string of 7 bases can comprises two codons (6)+1 base. The skilled artisan is well educated with respect to codon calculations.

According to a specific embodiment, the at least one of the identified strings comprise a coding sequence, and according to a specific embodiment, at least one of the identified strings comprises a non-coding sequence.

In embodiments of the invention in which the POI is endogenous to the cell, the string identified at 12 is preferably other than a string of a polynucleotide natively encoding the POI. In other embodiments the identified string may or may not be a string of a polynucleotide natively encoding the POI.

The method optionally and preferably continues to 13 at which the identified string is embedded in a transcript sequence encoding the POI. The embedding can be effected computationally thereby forming a computer readable transcript sequence that can be displayed or stored in a computer readable medium. In some embodiments of the present invention the embedding is effected experimentally. In this case, a biological molecule described by the identified string can be embedded in a biological molecule described by the transcript sequence. Also contemplated, are embodiments in which the embedding is effected experimentally (e.g., by nucleic acid ligation) to form an embedded transcript sequence, and a biological molecule described by the embedded transcript sequence is synthesized.

Once designed an expression construct comprising a polynucleotide expressing the artificial transcript and a promoter suitable for expressing the artificial transcript in the heterologous host can be cloned.

The method ends at 14.

The strings are preferably identified in the reference set by searching over the reference set a sequence of genetic elements that encodes the POI, such that it can be described by a concatenation of X subsequences of genetic elements that appear in the reference set. The searching is preferably by executing a computerized optimization algorithm that reduces or minimizes X. Representative examples of computerized optimization algorithms suitable for the present embodiments including, without limitation, a dynamic programming algorithm and a greedy algorithm. In various exemplary embodiments of the invention the search is subjected to a criterion according to which concatenation of longer subsequences is preferential over shorter subsequences. This can be achieved by weighing longer subsequences with higher weights than shorter sequences. In some embodiments of the present invention the search is subjected to a criterion according to which concatenation of subsequences that are more frequent in the reference set is preferential over subsequences that are less frequent in the reference set. This can be achieved by weighing the subsequences according to their repetition in the reference set. Other criteria are also contemplated.

Preferably, the method weighs the subsequences according to more than one criterion, e.g., both according to their length (higher weights for longer subsequences) and according to their repetition in the reference set (for example, higher weights for more frequent subsequences). For example, when two candidate subsequences are of equal lengths, the method selects the candidate that is more frequent in the reference set. Similarly, when two candidate subsequences appear in the reference set at the same frequency, the method selects the candidate that is longer.

In some embodiments of the present invention the method receives prior information regarding regulatory locus within the polynucleotide sequence. In these embodiment the search over the reference set is accompanied by a penalty-reward procedure based on the received prior information.

In various exemplary embodiments of the invention the search over the reference set is preceded by a preprocessing operation in which a suffix tree or a suffix array is constructed for the input reference set.

A suffix tree is a data-structure having branches stemming from a root with each branch terminating at a leaf node that encodes a suffix of a sequence in the reference set. Appended to each edge of the suffix tree is a label corresponding to a character string segment, and the arrangement of the labels appended to the edges descending from the root node to a leaf node is employed to define the pertinent leaf node as a suffix. A different first character may be provided for each label appended to each edge extending from a single node in the suffix tree, and the edges are sorted in accordance with the first character of each label.

Since the data size of a suffix tree is large, to reduce this size, a suffix array can be used as the data structure. A suffix array typically stores suffixes of the input reference set which are lexicographically sorted. The positions of the suffix array are optionally and preferably mapped to positions in the input reference set in order of appearance within the input reference set. A suffix array may be viewed as a compact representation of a suffix tree, so that when a suffix array is employed, compared with when a suffix tree is employed, the memory capacity required for a search mounted for a character string is reduced.

Thus, in some cases, a suffix array is preferred from the standpoint of computation memory usage, and a suffix tree is preferred from the standpoint of computation time (but this may be depended on the nature of the input and implementation).

The polynucleotides of the present embodiments encode a polypeptide of interest that is exogenous (heterologous) or endogenous to the host cell. The polypeptides may be intracellular polypeptides (e.g., a cytosolic protein), transmembrane polypeptides, or secreted polypeptides. Heterologous production of proteins is widely employed in research and industrial settings, for example, for production of therapeutics, vaccines, diagnostics, biofuels, and many other applications of interest. Exemplary therapeutic proteins that can be produced by employing the subject compositions and methods include but are not limited to certain native and recombinant human hormones (e.g., insulin, growth hormone, insulin-like growth factor 1, follicle-stimulating hormone, and chorionic gonadotropin), hematopoietic proteins (e.g., erythropoietin, C-CSF, GM-CSF, and IL-11), thrombotic and hematostatic proteins (e.g., tissue plasminogen activator and activated protein C), immunological proteins (e.g., interleukin), antibodies and other enzymes (e.g., deoxyribonuclease I). Exemplary vaccines that can be produced by the subject compositions and methods include but are not limited to vaccines against various influenza viruses (e.g., types A, B and C and the various serotypes for each type such as H5N2, H1N1, H3N2 for type A influenza viruses), HIV, hepatitis viruses (e.g., hepatitis A, B, C or D), Ebola virus, Lyme disease, and human papillomavirus (HPV). Examples of heterologously produced protein diagnostics include but are not limited to secretin, thyroid stimulating hormone (TSH), HIV antigens, and hepatitis C antigens.

Proteins or peptides produced by the heterologous polypeptides can include, but are not limited to cytokines, chemokines, lymphokines, ligands, receptors, hormones, enzymes, antibodies and antibody fragments, and growth factors. Non-limiting examples of receptors include TNF type I receptor, IL-1 receptor type II, IL-1 receptor antagonist, IL-4 receptor and any chemically or genetically modified soluble receptors. Examples of enzymes include acetlycholinesterase, lactase, activated protein C, factor VII, collagenase (e.g., marketed by Advance Biofactures Corporation under the name Santyl); agalsidase-beta (e.g., marketed by Genzyme under the name Fabrazyme); dornase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-beta), interferon gamma (IFNgamma), interferon gamma inducing factor I (IGIF), transforming growth factor beta (IGF-beta), RANTES (regulated upon activation, normal T-cell expressed and presumably secreted), macrophage inflammatory proteins (e.g., MIP-1-alpha and MIP-1-beta), Leishmnania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF alpha type II receptor, erythropoietin (EPO), insulin and soluble glycoproteins e.g., gp120 and gp160 glycoproteins. The gp120 glycoprotein is a human immunodeficiency virus (WIV) envelope protein, and the gp160 glycoprotein is a known precursor to the gp120 glycoprotein. Other examples include secretin, nesiritide (human B-type natriuretic peptide (hBNP)) and GYP-I.

Other heterologous products may include GPCRs, including, but not limited to Class A Rhodopsin like receptors such as Muscatinic (Musc.) acetylcholine Vertebrate type 1, Musc. acetylcholine Vertebrate type 2, Musc. acetylcholine Vertebrate type 3, Musc. acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykffin, C5a anaphylatoxin, Finet-leu-phe, APJ like, Interleukin-8 type A, Interleukin-8 type B, Interleukin-8 type others, C-C Chemokine type 1 through type 11 and other types, C—X—C Chemokine (types 2 through 6 and others), C-X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P(NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF, QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory 11 fam 1 through 13), Prostaglandin (prostaglandin E2 subtype EP 1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,11 GPR91, Purinoceptor P2RY5,8,9,10 GPR35,92,174, Purinoceptor P2RY12-14 GPR87 (JDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GAB A-B subtype 1, GAB A-B subtype 2, GABA-B like, Orphan GPRC5, Orphan GPCR6, Bride of sevenless proteins (BOSS), Taste receptors (TiR), Class D Fungal pheromone, Fungal pheromone A-Factor like (STE2,STE3), Fungal pheromone B like (BAR,BBR,RCB,PRA), Class E cAMP receptors, Ocular albinism proteins, Frizzled/Smoothened family, frizzled Group A (Fz 1&2&4&5&7-9), frizzled Group B (Fz 3 & 6), fizzled Group C (other), Vomeronasal receptors, Nematode chemoreceptors, Insect odorant receptors, and Class Z Archaeal/bacterial/fungal opsins.

Bioactive peptides may also be produced by the heterologous sequences of the present invention. Examples include, but are not limited to: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleulin, denileukin diftitox, interferon alfa-n3 (injection), interferon alfa-nl, DL-8234, interferon, Suntory (gamma-la), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphnmate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpimase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH (1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alphagalactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, ataciept, BR3-Fc, BN-003, BA-058, human parathyroid hormone 1-34 (nasal, osteoporosis), F-18-CCR1, AT-1100 (celiac disease/diabetes), JPD-003, PTH (7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH (1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In certain embodiments, the heterologously produced protein is an enzyme or biologically active fragments thereof. Suitable enzymes include but are not limited to: oxidoreductases, transferases, hydrolases, lyases, isomerases, and ligases. In certain embodiments, the heterologously produced protein is an enzyme of Enzyme Commission (EC) class 1, for example an enzyme from any of EC 1.1 through 1.21, or 1.97. The enzyme can also be an enzyme from EC class 2, 3, 4, 5, or 6. For example, the enzyme can be selected from any of EC 2.1 through 2.9, EC 3.1 to 3.13, EC 4.1 to 4.6, EC 4.99, EC 5.1 to 5.11, EC 5.99, or EC 6.1-6.6.

As used herein, the term "antibody" refers to a substantially intact antibody molecule.

As used herein, the phrase "antibody fragment" refers to a functional fragment of an antibody (such as Fab, F(ab')2, Fv or single domain molecules such as VH and VL) that is capable of binding to an epitope of an antigen.

According to one embodiment, the polypeptide of interest is of a bacterial, plant, yeast, algal, insect or mammalian origin for example a human polypeptide.

As used herein, the qualifier "heterologous" when relating to heterologous cells indicates that the species from which the cells are derived is not the same as the species of the polypeptide. For example, when the polypeptide has a human amino acid sequence, the cells in which it is expressed are non-human. Thus heterologous cells for the expression of human polypeptides include, but are not limited to bacterial cells (e.g. E. coli), fungal cells (e.g. S. cerevisiae cells), plant cells (e.g. tobacco), insect cells (lepidopteran cells), algal cells and other mammalian cells (Chinese Hamster Ovary cells).

Alternatively, heterologous may also refer to the expression of an endogenous gene in the native host cell, for which an artificial polynucleotide sequence has been designed to improve its expression in the native cell. In that sense, the transcript is implanted with at least one string of nucleotides which is non-native i.e., heterologous, to the natural transcript (but can appear in a different place in the genome).

The present teachings also refer to an artificial transcript having a nucleic acid sequence encoding a POI designed for expression in a heterologous host cell, the heterologous host cell being characterized by a reference set of polynucleotide sequences, the artificial transcript comprising at least one string of nucleotides being at least 4 nucleotides in length, the at least one string of nucleotides being embedded in the nucleic acid sequence to as to encode the POI, the at least one string of nucleotides being represented in the reference set of polynucleotide sequences, and wherein the at least one string of nucleotides and the nucleic acid sequence are heterologous and with the proviso that when the at least one string of nucleotides is a single string of nucleotides, the single string is not located at a 5' terminus of the nucleic acid sequence.

The present teachings also refer to an artificial transcript having a nucleic acid sequence encoding a POI designed for expression in a host cell, the host cell being characterized by a reference set of polynucleotide sequences, the artificial transcript comprising at least one string of nucleotides being at least 4 nucleotides in length, the at least one string of nucleotides being embedded in the nucleic acid sequence to as to encode the POI, the at least one string of nucleotides being represented in the reference set of polynucleotide sequences, and wherein the at least one string of nucleotides and the nucleic acid sequence are heterologous and with the proviso that when the at least one string of nucleotides is a single string of nucleotides, the single string is not located at a 5' terminus of the nucleic acid sequence.

According to a specific embodiment, the host cell is heterologous to the POI.

According to a specific embodiment, the host cell natively (endogenously) expresses the POI.

Alternatively or additionally the artificial transcript is obtainable according to the method described herein.

In any of the teachings the artificial transcript comprising the at least one string of nucleotides comprises at least two strings.

The string of nucleotides according to the present teachings is either heterologous or endogenous to the nucleic acid sequence which natively encodes the polypeptide of interest.

In this context heterologous refers to xenogeneic relationship between the string and the nucleic acid sequence. As used herein "endogenous" refers to naturally occurring within the cell from which the reference set of polynucleotide sequences is derived.

The collection of at least one string and the native nucleic acid sequence forms the artificial (i.e., synthetic-manmade) transcript.

According to an embodiment of the invention, when a plurality of strings are embedded in the transcript at least two of the strings of the plurality of the strings are embedded in a discontinuous manner. That is the strings do not form the entire nucleic acid sequence but rather a portion thereof and optionally some of the native nucleic acid sequence flanks the at least one string of the plurality of strings.

According to a specific embodiment, when a single string is embedded in the nucleic acid sequence, this string is not positioned at the 5' end of the nucleic acid sequence. In other words a ramp structure is not formed as taught by WO2011/111034, which is herein incorporated by reference in its entirety.

As used herein the term "discontinuous" refers to not continuous i.e., having interruptions or gaps which are composed of the native nucleic acid sequence.

As used herein "native nucleic acid sequence" refers to the transcript sequence which is natively used to generate the POI.

The length of the native nucleic acid sequences disrupting the string(s) may be from several bases (less than 10) to 100; 100-1000, 100-5000, 100-500, 500-5000, or even longer bases or a combination of same.

The native nucleic acid sequence may be optimized for expression using means which are well known in the art such as by using codon usage tables or software.

FIG. 8 is a flowchart diagram describing a method suitable for estimating the adaptiveness of a transcript sequence encoding a POI to the gene expression machinery in a host cell, according to some embodiments of the present invention. The transcript sequence can be heterologous to the cell or endogenous to the cell. The gene expression machinery can relate to any gene expression stage. For example, in some embodiments of the present invention the method estimates the adaptiveness of the transcript sequence encoding the POI to the translational machinery in the cell, and in some embodiments of the present invention the a method estimates the adaptiveness of the transcript sequence encoding the POI to the transcriptional machinery in the cell. In some embodiments of the present invention the method estimates the ability of the transcript sequence to improve folding and/or functionality of a protein.

The method of the present embodiments can be utilized for any type of cells, including, without limitation, a cell culture, a whole organism, or a part of an organism.

The method begins at 20 and continues to 21 at which the method receives as input a sequence describing the POI (e.g., a transcript sequence) and a reference set of sequences, where the reference set of sequences is indicative of the gene expression machinery of the host cell, as further detailed hereinabove.

The transcript sequence and reference set can be received from a local computer-readable storage medium or over a communication network. The transcript sequence is preferably a sequence of genetic material that is characteristic to the POI.

The method optionally and preferably continues to 22 at which for each of a plurality of positions along the transcript sequence, a list of strings is generated. Each of at least a few of the generated strings is composed of a plurality of genetic elements, wherein a genetic element can be selected from the group consisting of a nucleotide, a codon, a codon pair, and codon fragment. The generated strings are subsequences of the input transcript sequence, and are also subsequences of at least one sequence of the reference set.

A representative procedure for generating the list of strings can be as follows. Denoting the input transcript sequence by S, the reference set of sequences by G, and the total length of S by |S|, the method consider each position i along S and generates a list of candidate fragments $C_i^j$ of S extending between positions i and j of S, where j is an integer satisfying i+x≤j≤|S|, x being a positive integer (e.g., x=1 or x=2 or x=2 or x=3 or x=4, or more). For each candidate fragment $C_i^j$, the method determines whether or not $C_i^j$ exists as a subsequence in one or more of the sequences of G. The method accepts the candidate $C_i^j$ as a string if $C_i^j$ exists as a subsequence in one or more of the sequences of G, and rejects candidate $C_i^j$ if $C_i^j$ does not exist as a subsequence in any one of the sequences of G. The result of this procedure is a list of strings $\{s_i^j\}$.

Optionally and preferably, before checking existence or absence of $C_i^j$ in G, a suffix tree or a suffix array is constructed for the input reference set, as further detailed hereinabove. The advantage of this embodiment is that it allows fast search over the sequences of G. Thus, in this embodiment, the suffix tree or a suffix array are utilized for determining whether or not $C_i^j$ exists as a subsequence in one or more of the sequences of G.

The method preferably selects another position along S and repeats the above procedure to obtain another list of strings. Following one or more such repetitions a plurality of lists $\{s_i^j\}$ is obtained, each list characterized by a different starting position i.

At least one, more preferably each, of the generated strings optionally and preferably has a length which is above a predetermined threshold length. Typically, the threshold length is 2 genetic elements or 3 genetic elements or 4 genetic elements or 5 genetic elements or 6 genetic elements or 7 genetic elements or 8 genetic elements or 9 genetic elements or 10 genetic elements or 50 genetic elements or 100 genetic elements or 500 genetic elements.

Thus, according to some embodiments, the generated string comprises 2-100 or 2-1000 strings of genetic elements, according to some embodiments, the generated string is 4-1000 genetic elements in length, according to some embodiments, the generated string is 10-1000 genetic elements in length, according to some embodiments, the generated string is 4-500 genetic elements in length, according to some embodiments, the generated string is 4-100 genetic elements in length, according to some embodiments, the generated string is 4-50 genetic elements in length, according to some embodiments, the generated string is 7-30 genetic elements in length, according to some embodiments, the generated string is 10-30 genetic elements in length, according to some embodiments, the generated string is 15-30 genetic elements in length.

According to a specific embodiment, at least one of the generated strings comprises a codon fragment. According to a specific embodiment, the at least one of the generated strings comprise a coding sequence, and according to a specific embodiment, at least one of the generated strings comprises a non-coding sequence.

The method optionally and preferably continues to 23 at which each of at least a few of the lists is processed to select a string based on the length of string, thereby providing a processed list of strings $\{S_i^j\}$. The processed list $\{S_i^j\}$ is preferably defined such that it contains a single string from each list $s_i^j$. Thus, for example, $\{S_i^j\}$ can include one string from the list $\{s_1^j\}$ (if $\{s_1^j\}$ exits), one string from the list $\{s_2^j\}$ (if $\{s_2^j\}$ exits), etc.

Preferably, but not necessarily the method selects the longest string of each of the lists. Formally, this can be written as $S_i^j = \max_{j-i}\{s_i^j\}$. Other criteria for selecting the string from a particular list $\{s_i^j\}$, are also contemplated. For example, the method can select the nth longest string of the list (e.g., the second longest string, etc).

The method preferably continues to 24 at which at least one statistical measure is calculated for the processed list $\{S_i^j\}$. The statistical measure(s) is indicative of the adaptiveness of the transcript sequence to the gene expression machinery. Representative examples of statistical measures suitable for the present embodiments include, without limitation, mean length, median length, supremum length, infimum length, any combination thereof and any function (e.g., a linear function) thereof.

In some embodiments, the statistical measure is the mean length of the strings in the processed list $\{S_i^j,\}$. Formally, in these embodiments the statistical measure can be calculated using the following formula $\Sigma_i |S_i^j|/|S|$, where the summation $\Sigma_i$ is over all positions i in S.

The method ends at 25.

Figure 3A:
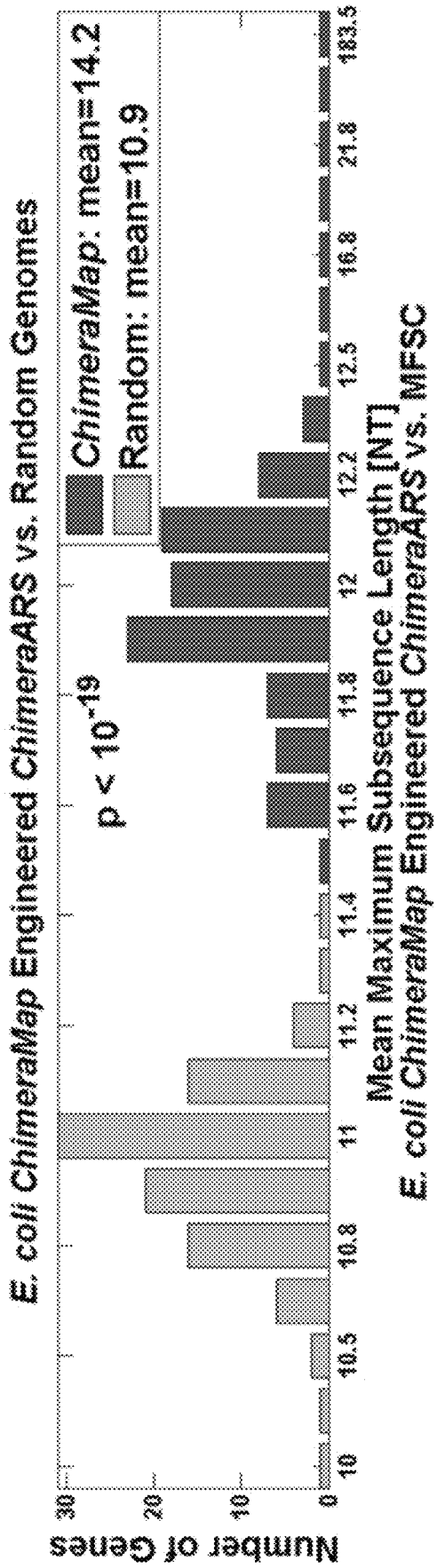
Figure 3B:
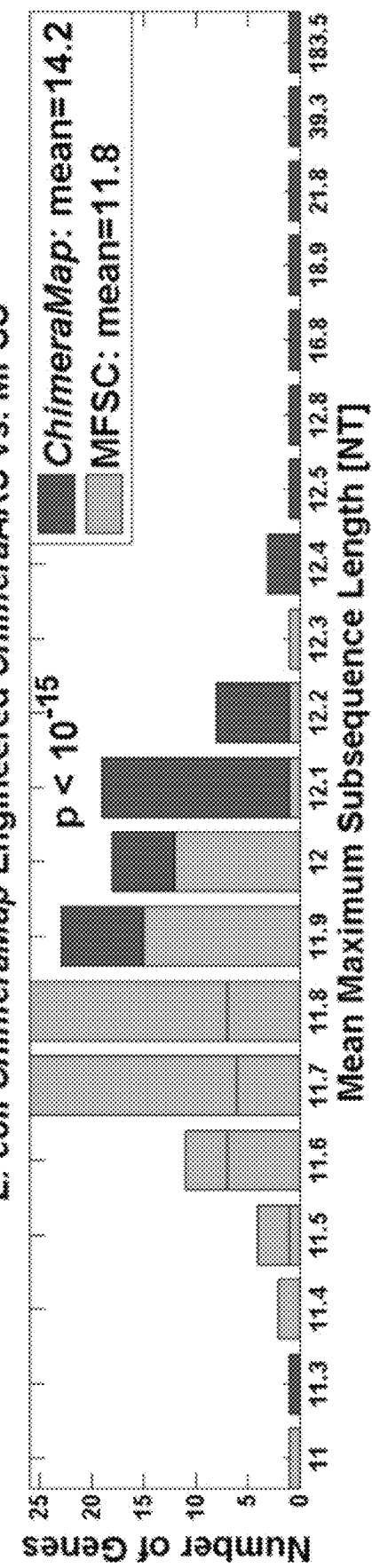

FIGS. 3A-B are schematic illustrations of a data processing system 30 according to some embodiments of the present invention. System 30 comprises a computer 32, which typically comprises an input/output (I/O) circuit 34, a data processor, such as a central processing unit (CPU) 36 (e.g., a microprocessor), and a memory 46 which typically includes both volatile memory and non-volatile memory. I/O circuit 34 is used to communicate information in appropriately structured form to and from other CPU 36 and other devices or networks external to system 30. CPU 36 is in communication with I/O circuit 34 and memory 38. These elements are those typically found in most general purpose computers and are known per se.

A display device 40 is shown in communication with data processor 32, typically via I/O circuit 34. Data processor 32 issued to display device 40 graphical and/or textual output images generated by CPU 36. A keyboard 42 is also shown in communication with data processor 32, typically I/O circuit 34.

It will be appreciated by one of ordinary skill in the art that system 30 can be part of a larger system. For example, system 30 can also be in communication with a network, such as connected to a local area network (LAN), the Internet or a cloud computing resource of a cloud computing facility.

In some embodiments of the invention data processor 32 of system 30 is configured for receiving the reference set and the POI via I/O circuit 34, and identifying in the reference set one or more sufficiently long strings of genetic elements that encode a portion of the POI, as further detailed hereinabove. Data processor 32 can also construct a suffix tree or a suffix array for the input reference set, as further detailed hereinabove. Optionally, the processor 32 computationally embeds the identified string in a transcript sequence encoding the POI, to provide a computer readable transcript sequence. The computer readable transcript sequence can be transmitted to memory 38 for storage and/or display 40 for displaying.

In some embodiments of the invention data processor 32 of system 30 is configured for receiving the reference set and the transcript sequence describing the POI via I/O circuit 34, and generating, for each of a plurality of positions along the transcript sequence, a list of strings, as further detailed hereinabove. Data processor 32 can also construct a suffix tree or a suffix array for the input reference set, as further detailed hereinabove. Optionally, data processor 32 is configured for processing the generated lists, to provide a processed list, and to calculate at least one statistical measure is for the processed list, as further detailed hereinabove.

In some embodiments of the invention system 30 communicates with a cloud computing resource (not shown) of a cloud computing facility, wherein the cloud computing resource receives the input and execute at least some of the operations described above with respect to processor 32.

The methods as described above can be implemented in computer software executed by system 30. For example, the software can be stored in or loaded to memory 38 and executed on CPU 36. Thus, some embodiments of the present invention comprise a computer software product which comprises a computer-readable medium, more preferably a non-transitory computer-readable medium, in which program instructions are stored. The instructions, when read by data processor 32, cause data processor 32 to receives the input and execute one or more of the methods as described above.

In any one of the embodiments described herein, the reference set of polynucleotide sequences can be selected from the group consisting of genomic DNA or RNA and ESTs.

According to a specific embodiment, the ESTs are cell-specific or tissue specific.

According to a specific embodiment, the reference set of polynucleotide sequences is normalized.

In order to express the polypeptides from the polynucleotides of the present embodiments in heterologous cell systems, the polynucleotides are ligated into nucleic acid expression vectors, such that the polynucleotide sequence is under the transcriptional control of a cis-regulatory sequence (e.g., promoter sequence).

As mentioned a variety of prokaryotic or eukaryotic cells can be used as host-expression systems to express the polypeptides of the present embodiments. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence, mammalian cells, insect cells and algal cells.

Below is a non-limiting description and examples of eukaryotic cells which can be used when implementing the present teachings.

Examples of eukaryotic cells which may be used along with the teachings of the embodiments include but are not limited to, mammalian cells, fungal cells, yeast cells, insect cells, algal cells or plant cells.

According to a specific embodiment, the cell is a cell line.
According to another specific embodiment, the cell is a primary cell.
According to a specific embodiment the cell is grown in suspension.
According to a specific embodiment, the cell is an adherent cell grown in a monolayer.
According to specific embodiments the cell is approved by the FDA or other regulatory agency for use in recombinant protein production for clinical purposes.
According to specific embodiments the cell is a mammalian cell.

The cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids. The cells may be derived from any developmental stage including embryo, fetal and adult stages, as well as developmental origin i.e., ectodermal, mesodermal, and endodermal origin.

Non limiting examples of mammalian cells include monkey kidney CV1 line transformed by SV40 (COS, e.g. COS-7, ATCC CRL 1651); human embryonic kidney line (HEK293 or HEK293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HeLa, ATCC CCL 2); NIH3T3, Jurkat, canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2), PER.C6, K562, and Chinese hamster ovary cells (CHO).

The CHO cells may include, but not be limited to, CHO/dhfr⁻ or CHO/DG44 cells. The Chinese hamster ovary tissue-derived CHO cell includes any cell which is a cell line established from an ovary tissue of Chinese hamster (*Cricetulus griseus*). Examples include CHO cells described in documents such as Journal of Experimental Medicine, 108, 945 (1958); Proc. Natl Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl Acad. Sci. USA, 77, 4216 (1980); Proc. Natl Acad. Sci., 60, 1275 (1968); Cell, 6, 121 (1975); Molecular Cell Genetics, Appendix I, II (pp. 883-900); and the like. In addition, CHO-K1 (ATCC CCL-61), DUXB11 (ATCC CCL-9096) and Pro-5 (ATCC CCL-1781) registered in ATCC (The American Type Culture Collection) and a commercially available CHO-S (Life Technologies, Cat #11619) or sub-cell lines obtained by adapting the cell lines using various media can also be exemplified.

According to a specific embodiment, the cell may be from a cell line used in hybridoma production.

According to specific embodiments the mammalian cell is selected from the group consisting of a Chinese Hamster Ovary (CHO), HEK293, PER.C6, HT1080, NS0, Sp2/0, BHK, Namalwa, COS, HeLa and Vero cell.

According to other specific embodiments the mammalian cell is a Chinese Hamster Ovary (CHO) cell or a HEK293 cell.

According to a specific embodiment the cell may be independently modified to include mutations which simplify the cloning and selection of an expressing cell, and/or increase the secretion or expression of the polypeptide of interest. Such modifications may take place for example in the carbohydrate pathway, in glutamine synthetase (GS) and/or in dihydrofolate reductase (DHFR) (see e.g. Estes and Melville, Adv Biochem Eng Biotechnol (2014) 139: 11-33, the contents of which are incorporated herein by reference in their entirety).

Constitutive promoters suitable for use with this embodiment of the present embodiments include sequences which are functional (i.e., capable of directing transcription) under most environmental conditions and most types of cells such as the cytomegalovirus (CMV) and Rous sarcoma virus (RSV).

Inducible promoters suitable for use with this embodiment of the present embodiments include for example the tetracycline-inducible promoter (Srour, M. A., et al., 2003. Thromb. Haemost. 90: 398-405) or IPTG.

The expression vector according to this embodiment of the present embodiments may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present embodiments include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression vector in order to increase the translation efficiency of a polypeptide expressed from the expression vector of the present embodiments. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present embodiments include those derived from SV40.

In addition to the elements already described, the expression vector of the present embodiments may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Expression vectors containing regulatory elements from eukaryotic viruses such as retroviruses can also be used by the present embodiments. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al., (1984) Nature 310:511-514], or the coat protein promoter to TMV [Takamatsu et al., (1987) EMBO J. 6:307-311] can be used. Alternatively, plant promoters such as the small subunit of RUBISCO [Coruzzi et al., (1984) EMBO J. 3:1671-1680 and Brogli et al., (1984) Science 224:838-843] or heat shock promoters, e.g., soybean hsp17.5-E or hsp17.3-B [Gurley et al., (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Various methods can be used to introduce the expression vector of the present embodiments into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6):

504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present embodiments. Such a medium typically includes an aqueous solution having assimilable carbon, nitrogen and phosphate sources, and appropriate salts, minerals, metals and other nutrients, such as vitamins. Cells of the present embodiments can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present embodiments can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range but also out of the range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al., (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al., (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Description of the Exemplified Approach

The technique of the present embodiments is based on the idea that various aspects of gene expression (mentioned above) are encoded in the transcript and specifically the ORF; thus, these "codes" (information) are frequently repeated in the coding sequences of the organism; in addition we expect to see more of these "codes" in genes (both heterologous and endogenous) that are highly expressed and/or more tightly regulated. Moreover, based on this idea the expression levels (and/or functionality and/or folding, etc.) of a heterologous or endogenous gene can be improved by engineering its subsequence's composition (including its codons) such that they are similar to the ones that appear in the endogenous genes of the host. This can be done in more than one way.

In some embodiments of the present invention a measure for the adaptation of the coding sequence to the intracellular gene expression regulatory machinery is defined. This measure is referred to below as Chimera Average Repetitive Substring and is abbreviated ChimeraARS.

In some embodiments of the present invention heterologous or endogenous genes are designed based on the genome of the host. A computer implemented procedure for such a design is referred to herein as ChimeraMap. Optionally and preferably the ChimeraMap procedure is executed without prior knowledge and is based only on the genome of the host, but can optionally include any type of prior knowledge.

Following is a more detailed description of ChimeraARS and ChimeraMap.

Figure 2A:
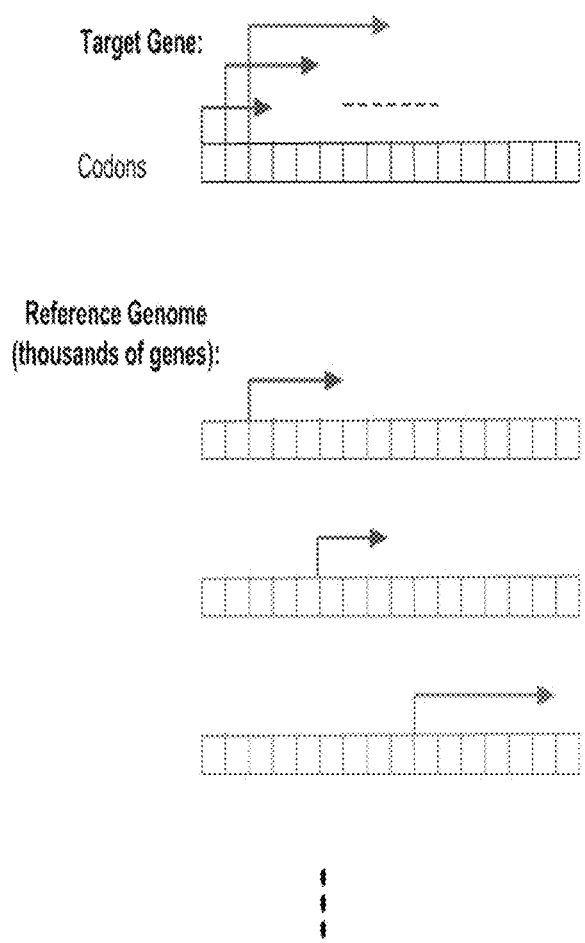

The ChimeraARS according to some embodiments of the present invention is depicted in FIGS. 2A and 10. A given POI P (e.g., a protein), can be described as a sequence of codons, S. The ChimeraARS score of the present embodiments is based on the tendency of subsequences in S to appear in a reference set of genes G. The set G can be constructed in more than one way, including, without limitation, considering only highly expressed genes, tissue specific genes, or genes with a certain function or property.

For simplicity and demonstrating the advantage of the technique of the present embodiments it is assumed, without loss of generality, that G includes the entire genome. The ChimeraARS measure is based on the observation made by the present inventors that evolution shapes the organismal coding sequences to improve their interaction with the intracellular gene expression machinery. Thus, if longer subsequences of S tend to appear in the organism's ORFs, the ChimeraARS measure is indicative that P is more optimized to the intracellular gene expression machinery, and thus probabilistically more highly expressed. The computation of the ChimeraARS score, ChimeraARS(G,S), of coding sequence S given reference genome G optionally and preferably includes one or more of the following operations (FIG. 2A, further details in the Methods section, below:

1) For each position i in the coding sequence S, find the longest subsequence $S_i^j$ that starts in that position and ends at position j, and also appears in at least one of the sequences of the genome G.

2) Let |S| denote the length of a sequence S. The ChimeraARS score of S is optionally and preferably defined based on the lengths of two or more of (e.g., all) the subsequence $S_i^j$. For example, the ChimeraARS score can be calculated as the mean length of two or more of (e.g., all) the subsequence $S_i^j$. In this embodiment, the ChimeraARS score is calculated as $\Sigma_i |S_i^j|/|S|$ where the summation $\Sigma_i$ is over all positions i in S.

As demonstrated in the following subsections, the ChimeraARS exploits information that does not appear in single codon distributions. Thus, among others, it can be used for estimating the adaptation of the codon content of a gene to the cellular gene expression machinery; as highly expressed genes are expected to be more adapted it can specifically be used for predicting the polypeptide expression (e.g., protein) of a gene from its codon distribution, while considering the multidimensional distribution of codons.

Figure 2B:
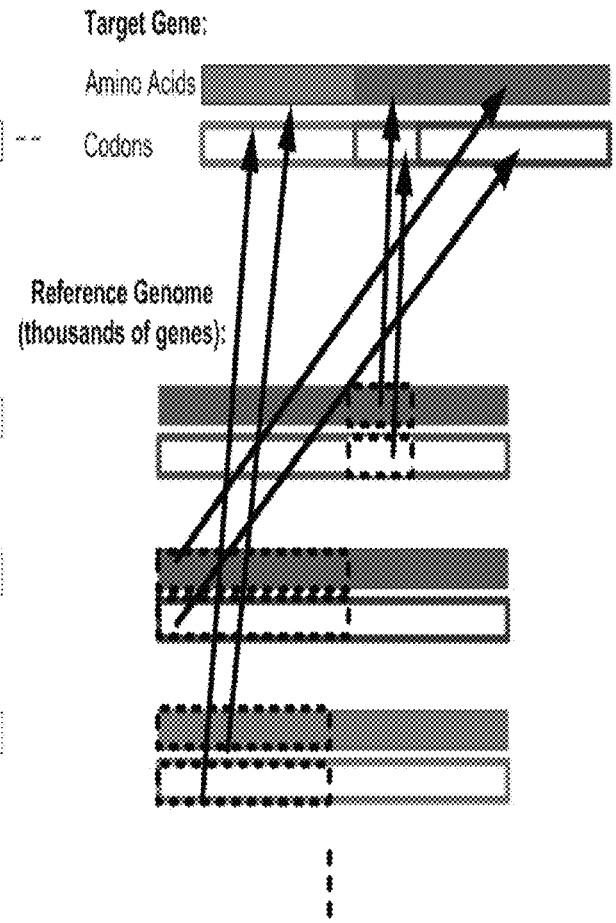

The objective of the ChimeraMap computer implemented procedure, according to some embodiments of the present invention, is schematically illustrated in FIGS. 2B and 11 (further details in the Methods section). Given a target POI (e.g., protein) P, whose coding sequence is S, and a reference set of genes G (e.g., the entire genome, a part of the genome, a part of the transcriptome, etc.), the ChimeraMap procedure finds at least one string of nucleotides (S*) that codes P but is composed of codon or nucleotide blocks that are more frequent in G than other codon or nucleotide blocks.

When several blocks of the same length exist in G, the ChimeraMap optionally and preferably selects one of the blocks, more preferably the most frequent block so as to further improve the adaptiveness of S* to G. In various exemplary embodiments of the invention ChimeraMap minimizes the number of such 'codon/nucleotide blocks' in S*. For example, the ChimeraMap can find blocks which are as long as possible, thereby minimizing the number of blocks; minimizing the number of such blocks is a major point of the ChimeraMap algorithm. Optionally and preferably S* is composed of non-overlapping codon or nucleotide blocks. But overlapping codon or nucleotide blocks are also contemplated.

The ChimeraMap computerized procedure can be used for optimizing the coding sequence of heterologous genes for expressing them in a new host but also for optimizing/maximizing the expression of endogenous genes. Under this construction, the boundaries between blocks are the only regions with codon or nucleotide sequences that may not appear in the host genome. The ChimeraMap minimizes these regions by minimizing the number of 'codon/nucleotide blocks'. Since the 'codon/nucleotide blocks' already appear in the host genome they are expected to be compatible with the host gene expression machinery. The boundaries between blocks, on the other hand, correspond to subsequences that do not appear in the host genome, thus they may not be compatible with the host gene expression machinery and ChimeraMap minimizes them.

The performance and properties of the ChimeraARS and ChimeraMap as delineated above are described in greater detail in the following subsections.

Properties of the Procedure and Score

All the details regarding the computation of the ChimeraARS score and the ChimeraMap output appear in the Methods section, below.

In various exemplary embodiments of the invention the calculation of the ChimeraARS score includes a preprocessing operation of generating a suffix tree or array of all the coding sequences of the reference set G. Based on this suffix tree, all the longest subsequences of the target P can be computed, resulting in a total running time complexity of $O(|O|+|P|)$, see Methods for more details.

The same or similar preprocessing operation can be employed by the ChimeraMap computerized procedure, except that this procedure also includes an optimization algorithm, such as, but not limited to, a dynamic programming algorithm or a greedy algorithm that finds the optimal solution with a total running time complexity of $O(|G|+|P|)$, see Methods for more details.

Some properties of ChimeraARS and the ChimeraMap objective can be shown by universal information theoretic approaches for compressing Markovian sequences, estimating the number of bits needed for describing a first sequence (S, in the present example) given a second sequence (G, in the present example) [28-32]. Formally, let $x^n$ denote a codon or nucleotide sequence of length n. Specifically, if the codon or nucleotide distribution in G and S are generated by Markovian processes with probability distributions $M_S$ and $M_G$, respectively, the score ChimeraARS(G,S) estimates the following measure:

$$\text{ChimeraARS}(G,S) \approx \log(|G|)/(-E_{M_S} \log(M_G)) \quad \text{(EQ. 1)}$$

where $$-E_{M_S} \log(M_G) = \lim_{n \to \infty} (1/n) \Sigma_{x^n} M_S(x^n) \log(1/M_G(x^n)) \quad \text{(EQ. 2)}.$$

When the distributions of S and G are similar, S can be better compressed by G. When $M_S = M_G$ the score ChimeraARS(G,S) (EQ. (1)) converges to $\log(|G|)/H(M_S)$ where $H(M_S)$ is the entropy of $M_S$, and, according to EQ. 2, $H(M_S)$ is smaller than $-E_{M_S} \log(M_G)$ for $M_S \neq M_G$.

Genes designed according to the ChimeraMap computerized procedure typically have higher ChimeraARS scores. The ChimeraMap computerized procedure engineers the genetic sequence (e.g., coding sequence, transcripts, UTRs, introns, etc.) of the target gene such that it includes relatively long subsequences that appear in the reference set G. The ChimeraARS score detects the tendency of a genetic sequence to include relatively long subsequences that appear in the reference set G, and thus, among others, its adaptiveness to the genome's gene expression machinery.

The following analysis further demonstrates this relation. 100 E. coli genes were uniformly selected according to their protein abundance (PA) levels. Several variations of the selected genes were created. In a first variation, 100 randomizations of the genes while maintaining the encoded protein, the amino acid bias, and the codon usage bias per gene were performed. In a second variation, the genes were optimized according to the CAI rationale, replacing every synonymous codon with its most abundant version, referred to herein as the Most Frequent Synonymous Codon (MFSC), a variation representing the encapsulation of single codon distribution. In a third variation, the genes were engineered according to the ChimeraMap procedure of the present embodiments. The results of this analysis are shown in FIGS. 3A and 3B.

FIG. 3A shows the ChimeraMap engineered genes' ChimeraARS scores, as compared to those of the averaged 100 randomizations, of the E. coli subset of genes (14.2 vs. 10.9). Performing a Wilcoxon signed rank test a p-value<$10^{-19}$ was obtained. FIG. 3B shows the ChimeraMap engineered genes' ChimeraARS scores, as compared to those of the MFSC version (14.2 vs. 11.8). Performing a Wilcoxon signed rank test, a p-value<$10^{-15}$ was obtained. FIGS. 3A-B demonstrate that the ChimeraMap engineered genes obtain significantly higher ChimeraARS scores compared to both the randomized and MFSC versions.

High Dimensional Information is Encoded in the Codon Usage Bias and can be Exploited by the Chimera Approach The present inventors successfully demonstrated that high dimensional information appears in the coding sequences of organisms. This was achieved by comparing the ChimeraARS scores of endogenous E. coli genes to the ones obtained for randomized genomes that maintain the protein content and frequencies of single codons. If indeed patterns of subsequences of codons or nucleotides (longer than one) tend to repeat in the endogenous genome more than expected by chance, the ChimeraARS scores will tend to be higher in the real genome in comparison to the randomized genome.

In order to compute the ChimeraARS measure for endogenous genes, for each gene instead of using the entire genome, all the genes excluding the current were considered as the reference genome. First, the ChimeraARS measure was computed for the real and randomized E. coli genome. The randomized genome encoded the same protein and single codon frequencies in each gene as in the original E. coli genome. However, it did not include the same higher dimensional distributions (further details in the Methods section). For each gene, the respective ChimeraARS score was calculated as the mean over the maximum subsequence length of each of its codon or nucleotide positions that can be found in all the other genome genes.

Figure 4A:
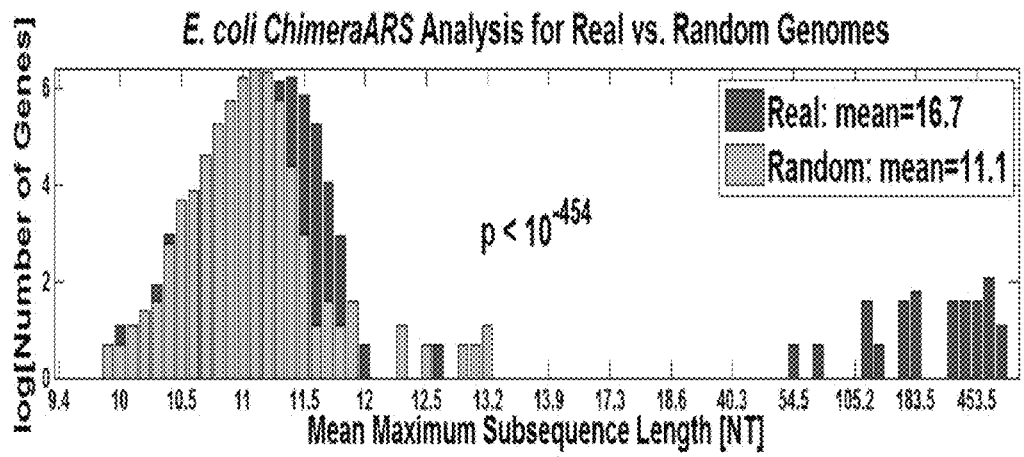
Figure 4B:
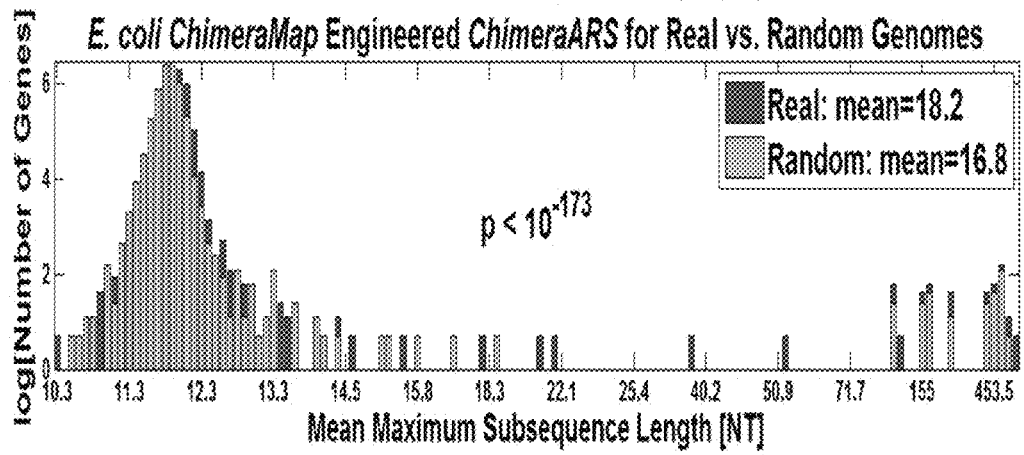
Figure 4C:
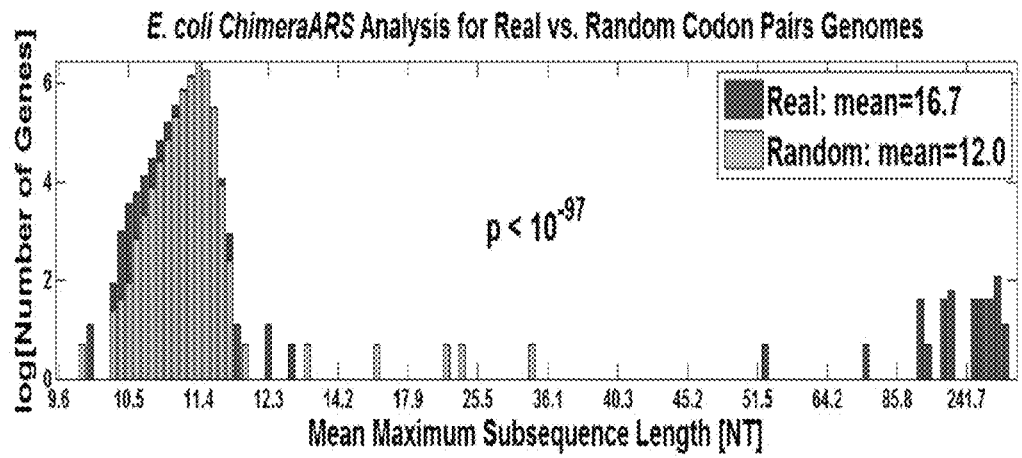

The results of this test are shown in FIGS. 4A-C.

FIG. 4A shows the ChimeraARS scores for the real and randomized E. coli genome. The mean ChimeraARS score for the real genome was significantly higher than the random (16.7 vs. 11.1). Performing a Wilcoxon signed rank test, a p-value<$10^{-454}$ was obtained.

The result shown in FIG. 4A supports the conjecture by the present inventors that long subsequences of codons or nucleotides tend to appear in the coding sequences of the analyzed organism more than expected by chance. Thus the present analysis supports the hypothesis that at least some of the repetitive codon subsequences affect the fitness of *E. coli*.

Further analyses described below support the conjecture by the present inventors that this high dimensional information is related at least partially to gene expression regulation, as ChimeraARS scores correlate with the expression levels of endogenous and heterologous genes.

An additional validation was directed to the verification that the engineered genes which the ChimeraMap algorithm produces maintain the noted higher length distribution, and that it is higher than the one obtained for randomized genomes also in this case. To this end, taking each gene as a target, its ChimeraMap version, which encodes the same protein, but is composed of the maximal most frequent subsequences in all the other genes of the genome (excluding the current gene), was built. This was performed for the real and randomized *E. coli* genome respectively.

FIG. 4B shows the ChimeraARS scores for the *E. coli* real and random genome, as engineered by the ChimeraMap procedure of the present embodiments. The mean ChimeraARS score for the ChimeraMap engineered real genome was significantly higher than that of the engineered random genome (18.2 vs. 16.8). Performing a Wilcoxon signed rank test, a p-value$<10^{-237}$ was obtained. The increase in the ChimeraARS scores relatively to those shown in FIG. 4A is due to the fact that genes designed by the ChimeraMap procedure tend to include longer repetitive subsequences that appear in the host genomic coding sequences, and thus result in higher ChimeraARS scores. This phenomenon can be seen in the random genome as well, further demonstrating the ability of the ChimeraMap procedure to design genes. In both analyses paralogs were removed in-order to show that the reported signal cannot be attributed to sequence similarity among paralogs.

FIG. 4C shows ChimeraARS scores for the real and randomized *E. coli* genome which maintains the codon pairs distribution, in addition to the single codon distribution and encoded protein. The mean ChimeraARS score for the real genome was significantly higher than the random (16.7 vs. 12). Performing a Wilcoxon signed rank test, a p-value$<10^{-97}$ was obtained.

These results further substantiates the conjecture that long subsequences of codons or nucleotides do tend to appear in the coding sequences of the analyzed organism more than expected by chance, and that the ChimeraMap algorithm can exploit this information.

Measures Based on the Chimera Approach Correlate with Various Aspects of Gene Expression and Include Information that does not Appear in Conventional Codon Usage Bias Measures A further analysis was directed to show that the repeated subsequences, and the ChimeraARS score, are related to the expression levels of endogenous genes. To this end, the correlation obtained between the CAI [21] (a measure based on the independent distribution of single codons; see details in the Methods section) and measurements related to various gene expression aspects/stages (mRNA levels, ribosomal density, and protein levels), were compared to the one obtained based on a regressor of both the CAI and ChimeraARS. The analysis was based on cross validation and control for the number of features in the regressor/predictor; more details in the Methods section.

The results of the analysis are shown in FIGS. 5A-F, where FIGS. 5A-C are dot plots, and FIGS. 5D-F are histograms of adjusted Spearman correlations. Shown in FIGS. 5A-F are prediction of (i) a regression model which is based only on the CAI (gray), and (ii) a model which is based on the CAI and ChimeraARS (pale blue), vs. measured protein abundance (A,D), mRNA levels (B,E), and ribosomal density (C,F), respectively.

As shown, the correlation with gene expression increases when adding the ChimeraARS feature relatively to regression based on the CAI alone, also when controlling for the number of features by computing adjusted correlations (see Methods). This result supports the conjecture that the ChimeraARS score of the present embodiments infers information related to expression levels which cannot be detected by conventional approaches such as the CAI. Thus, information related to gene expression regulation is encoded in high-dimensional distributions of codons and nucleotides in the coding sequence.

Analyses of Heterologous Gene Expression by the Chimera Approach Demonstrate its Advantages Over Conventional Codon Usage Bias Measures Goodman et al., [23] recently designed a heterologous gene library utilizing the first 11 amino acids including the initiating methionine from 137 essential genes in *E. coli*. The authors generated 13 variants of each gene, where they changed the synonymous codons used to encode the peptide, always keeping the start codon as ATG. Using two promoters, and four RBSs (Ribosome Binding Site) they generated 14,234 heterologous gene sequences, and measured their translation rates. Goodman et al., show that there is no correlation between the CAI [21] and the translation rate.

The present inventors successfully showed that the ChimeraARS of the present embodiments correlates with the translation rates of the Goodman et al., experiment.

Analyzing the heterologous *E. coli* data of Goodman et al., [23], using as a reference genome the first 11 codons of each endogenous *E. coli* gene (such that it corresponds to the first 11 codons that were modified in the heterologous gene library), the present inventors calculated the ChimeraARS score for each of the heterologous 11 codon long coding sequences. The correlation of the Goodman et al., translation rates was calculated with the ChimeraARS score, and compared to the ones achieved for the CAI.

FIGS. 6A-H show the Spearman correlation between the ChimeraARS score and the CAI respectively with the Goodman et al., translation rates, according to their promoter (High/Low), and RBS (ribosomal binding site; Strong/Weak/Mid/WT) gene groups (High promoter and Mid RBS in FIG. 6A, High promoter and Strong RBS in FIG. 6B, High promoter and Weak RBS in FIG. 6C, High promoter and Wild-Type RBS in FIG. 6D, Low promoter and Mid RBS in FIG. 6E, Low promoter and Strong RBS in FIG. 6F, Low promoter and Weak RBS in FIG. 6G, Low promoter and Wild-Type RBS in FIG. 6H). Linear regression lines are also shown, although the relations are monotone but not linear.

These results demonstrate that, while the CAI does not correlate with the translation rate of the heterologous gene library (correlation between −0.34 and 0.09; and mostly not significant; where the negative correlation is in the wrong direction), the ChimeraARS score of the present embodiments correlates well the translation rate of the heterologous gene library (correlation generally between 0.3 and 0.67; p<0.02). These results thus demonstrate that the ChimeraARS score of the present embodiments can detect the expression of genes also in heterologous systems. In addition, the results support the conjecture by the present inventors that the relation between the ChimeraARS score and expression levels described above is at least partially causal or direct, wherein higher ChimeraARS scores contribute to higher expression levels. These results also support the conjecture by the present inventors that the ChimeraMap procedure of the present embodiments is capable of optimizing expression levels of genes, because genes designed by the ChimeraMap procedure have higher ChimeraARS scores.

Methods

Datasets

Coding Sequences: The *E. coli* genome was downloaded from the NCBI ftp site.

Protein Abundance: *E. coli* protein abundance measurements were downloaded from PaxDB [24].

Heterologous gene sequences and expression: *E. coli* Heterologous gene sequences, their corresponding measured translation rates, and CAI values, were taken from Goodman et al., [23].

Ribosomal density: *E. coli* ribosomal density was downloaded from [8]; this data includes ribosomal densities at a single nucleotide resolution for each ORF; we averaged this data to get the ribosomal density per ORF.

The ChimeraARS Score and the ChimeraMAP Procedure

Let P denote a POI (e.g., a heterologous or an endogenous polyprotein), which is a sequence of amino-acids of length|P|, let $P_j^k$ denote the subsequence of amino acids in positions j to k in P, and let c(P) denote the sequence of codons or nucleotides corresponding to a POI P (for example, $c(P_j^k)$ includes the codons of amino acids j to k in P).

The ChimeraARS score estimates the optimality of the codons or nucleotides of a gene to the intracellular gene expression machinery of its host via the tendency of its sequence data (e.g., ORF, transcripts, UTRs, introns, etc.) to include long subsequences of codons or nucleotides that appear in a certain reference set of genes or genetic elements. For each position j of P, the largest kj (denoted by kj*) is computed such that the subsequence $c(P_j^{kj}*)$ appears in the sequence data (genes, proteins, or any genetic element) of the host.

In some embodiments of the present invention the ChimeraARS score is the mean length of these subsequences: $\text{mean}_j c(P_j^{kj}*)$.

In some embodiments of the present invention the ChimeraARS score is calculated based on lengths in amino acids, and describes the tendency of a protein to include subsequences of amino acids that appear in other proteins.

In some embodiments of the present invention the ChimeraARS score is calculated based on length in codons, and describes the tendency of a coding sequence to include subsequences of codons that appear in other coding sequences.

In some embodiments of the present invention the ChimeraARS score is calculated based on length in nucleotides, and describes the tendency of a coding sequence to include subsequences of nucleotides that appear in other coding sequences.

While certain embodiments of the present invention are described with a particular emphasis to calculations based on length in nucleotides, it is to be understood that the calculations of the score can be based on any type of genomic element, including, without limitation, transcripts, UTRs, introns, genes and the like.

The ChimeraMAP procedure constructs the sequence elements (e.g., codons, nucleotides) of a POI P such that it fits the machinery of the cell.

Thus, the ChimeraARS provides a measure of the coding sequence's adaptiveness to the gene-expression intracellular machinery, and the ChimeraMap provides a new optimized coding sequence that encodes the same protein as the original one.

Specifically, the objective of the ChimeraMap procedure is optionally and preferably to find a sequence of genetic elements (e.g., codons, nucleotides) that encodes P as c*(P), such that it can be described by a concatenation of as few as possible most frequent subsequences of genetic elements (e.g., codons, nucleotides) that appear in the coding sequences of the host genome. In some embodiments of the present invention the subsequences are as long as possible, and the genomic element (e.g., codons, nucleotides) sequence selected is the most frequent of all the equal length contenders.

The biological motivation on which the objective is defined is the fact that genes in the reference genome of the host are expressed well in the host, and therefore the coding sequences of these genes do not include subsequences that down regulate them. The ChimeraMap procedure employs an objective function that minimizes the regions which include genomic element (e.g., codons, nucleotides) sequences that do not appear in the host. This can be achieved by covering the target coding sequence with as few as possible subsequences of genomic element (e.g., codons, nucleotides) that appear in the host coding sequences (see, for example, FIG. 2B).

The calculation of the ChimeraARS score optionally and preferably includes a preprocessing operation in which a suffix tree or a suffix array is constructed for the coding sequences of the host genome [33, 34]. This can be done in O(|G|) where |G| is the length of the reference sequences of the host. Usually, a suffix array is preferred from the standpoint of computation memory usage, and a suffix tree is preferred from the standpoint of computation time.

When a suffix tree is constructed, the length of the longest subsequence starting at each position in the target gene that appears in the host genome can be found in an efficient manner in O(|P|) (see [34], matching statistics algorithm, pp 132-134), so the total time complexity of the algorithm is O(|G|+|P|).

The ChimeraMap procedure optionally and preferably includes a dynamic programming (DP) algorithm that builds an optimized representation of P, maintaining the encoded element to that of a specified reference set G, by minimizing the number of subsequences from the reference genome required to cover it. When this problem is solved naively, it is essentially exponential. The ChimeraMap procedure of the present embodiments reduces this to polynomial or linear time based on the observation that the optimal solution can be greedily extended in each DP step.

Similarly to the ChimeraARS, the preprocessing step of the algorithm is based on building a suffix tree for the coding sequences (or any definition of a reference genome) of the reference set in time O(|G|).

The procedure optionally and preferably considers only the previous step in the DP optimal solution space.

In the ith step of the DP, the length i of the substring of P that is considered grows by 1, with i being from 1 to |P|. The DP determines the optimal solution for the ith step i based on the solution at step (i−1). The manner in which the ChimeraMap procedure tries to elongate the previous optimal solution to length i is as follows. Each optimal solution is represented by a list of pairs of numbers, symbolizing the start and end positions of the substrings (blocks) covering P up to that point (FIG. 2B). The ChimeraMap procedure looks at the last such block ([start end]) and tries to find a match in the suffix tree of G for P(start:i), and if that fails for P(end+1:1).

In some embodiments of the present invention a pointer to the end of solution i−1 in the suffix tree is maintained, so that the determination whether there is a match for P(start:i) can be made O(1) by continuing the down traversal on the current edge to the next character. If a match is found the search is completed, otherwise a pointer is kept to the root of the tree and the search begins for P(end+1:i) in constant time. Thus, a total time complexity of O(|G|+|P|) is obtained.

The present inventors found that there exists a maximal length for a covering substring from a reference set. Let lcsMAX denote the length of the longest substring that is common to P and G. lcsMAX can be calculated using the common suffix tree of P that is found in G and all its prefixes. If the sequences G and P are generated by a Markov process O(lcsMAX) is expected to be of the order of O(log|G|). In an analyzed organism|G| equals 3,958,573, the log of which is 15.2, while the mean lcsMAX is 15.3 with an STD of 38.

Optimality

Following is a proof that the ChimeraMap procedure finds an optimal solution with induction, n=|P|. The base case is i=1. The procedure initiates with the first character of P. The first solution is therefore the block [1,1] which is optimal. For the inductive step or the proof optimality is assumed for i=n−1. We assume we have optimal solutions for all the algorithm steps up to n−1. The proof for i=n is as follows.

The algorithm at each step looks back at the previous solution, and elongates it according to the following rule: look at the last mapped block ([start end]) of the solution and try to find a match in the suffix tree for P(start:i), and if that fails for P(end+1:i). If a match is found, merge to the current previous solution in the appropriate manner. For each solution, the procedure either elongates its last block, thus not increasing the number of substrings covering P, and since that solution was optimal, so is the solution for i. If an existing block cannot be elongated, a new block [end+1 i] is opened, thus increasing the previous optimal solution by one. If an existing block could have been elongated, this solution is chosen as the optimal for step i. If not, the optimal solution grows by no more than one.

Now, assume that the optimal solution of step i=n includes l blocks. It is assumed that the algorithm found all the optimal solutions for i<n, and it finds the optimal solution for i=n. Since the optimal solution of i=n includes l blocks, the optimal solution for i=n−1 includes either l−1 or l blocks. If it is of length l−1, then no extension of the last block exists, and the algorithm adds a new block to the ith solution. If it is of length l blocks, this means that an extension exists. Assumes by negation that the last block of the solution i=n−1 is of length w and represents the string α, and cannot be extended. Thus, since according to the assumption the optimal solution for the ith step includes l blocks there must be a block representing the string β of length longer than w that can be extended. But a is a suffix of β and therefore can also be extended, contradicting the negation assumption.

Genomic Randomization

The *E. coli* genome randomization maintaining the encoded protein, the codon bias distribution and the amino acid bias distribution was performed as follows: for each gene, the synonymous codons of its coding sequence were permuted (within the respective synonymous groups). The significant results obtained based on this randomization are very strong as the randomization maintains many fundamental properties of the original genome including: 1) the protein encoded in the genome and 2) the codon frequencies of each gene.

Codon Adaptation Index (CAI)

The CAI [21] is a technique for analyzing codon usage bias, by measuring the deviation of a given protein coding gene sequence with respect to a reference set of genes. Ideally, the reference set in CAI is composed of highly expressed genes, so that the CAI provides an indication of gene expression levels under the assumption that there is translational selection to optimize gene sequences according to their expression levels.

In the present example, the CAI was calculated based on the entire genome (the reference set) for the endogenous analysis. The CAI values for the heterologous analysis were taken from [23].

Regression Analysis

In order to demonstrate that the ChimeraARS score captures expression information not modeled by the CAI (as a representative of single codon usage bias modeling), a ranked linear regression analysis using Spearman correlation was performed with a two-fold cross-validation repeated 100 times. In addition, the adjusted correlation was calculated at each cross-validation iteration to account for the number of features (see, for example, [36]), basing this scheme on the CAI alone, and then on both the CAI and ChimeraARS.

Discussion

The present Example describes a computational approach named Chimera for exploiting high dimensional information related to gene expression that is interleaved in the redundancy of the genetic code, and for engineering coding regions (or any other genomic entity) of heterologous or endogenous genes without prior knowledge. The approach presented in this example is based on an information theoretic technique for data compression, and was found to be very efficient in terms of computational running time.

Figure 1:
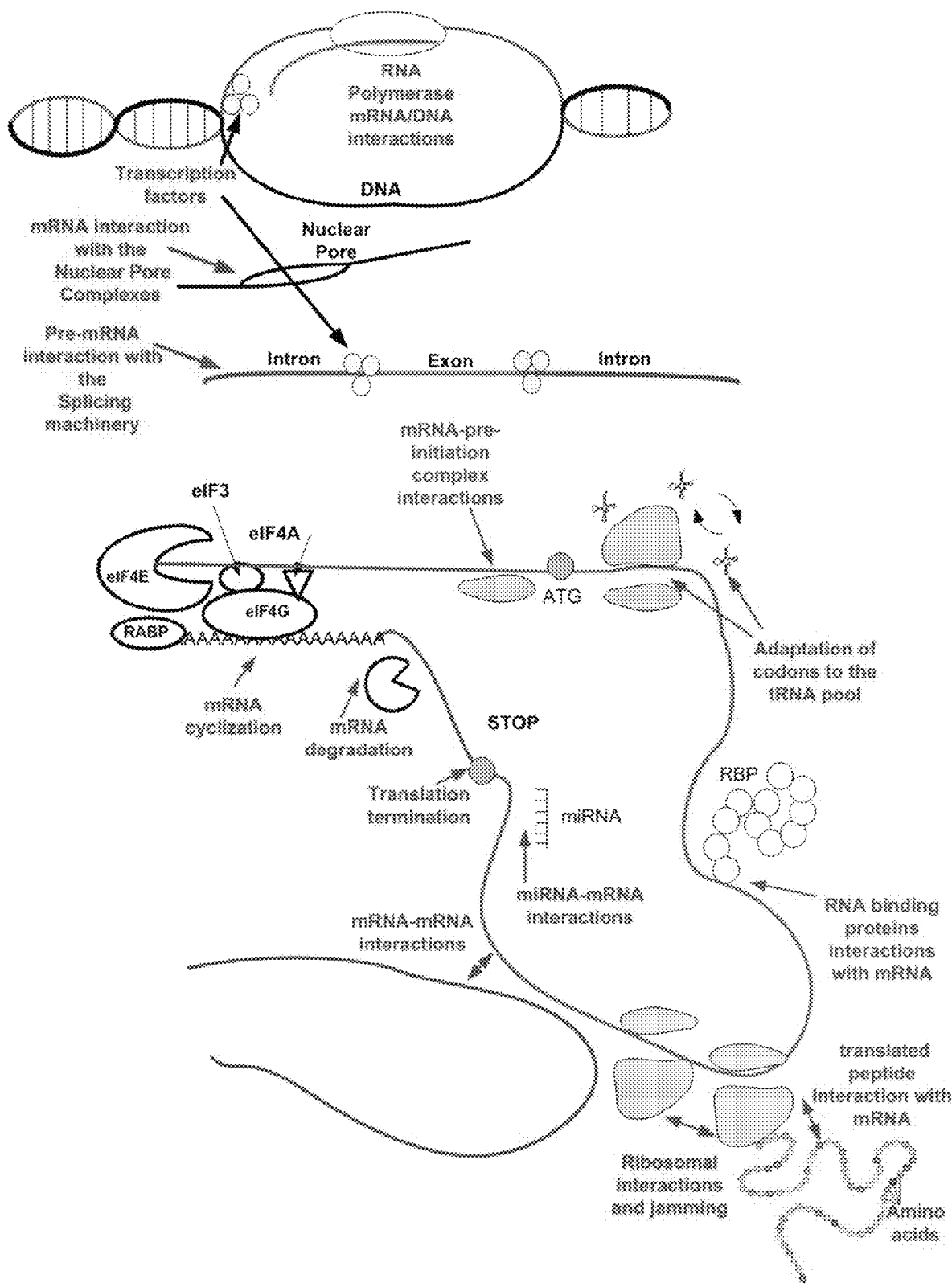

In this Example, *E. coli* was analyzed since this is an organism with large scale measurements of both heterologous and endogenous gene expression data. Some embodiments of the present invention are suitable for other organisms, such as, but not limited to, eukaryotes, and specifically multi-cellular organisms such as plants. There are different stages of gene expression, including many types of interactions with the mRNA molecules that occur only in these groups of organisms. For example, splicing, interaction with the nuclear pores, and regulation by miRNA (see FIG. 1), occur only in eukaryotes. These examples include interactions between the intracellular machinery and the mRNA molecule, and are at least partially encoded, for example, in the ORF via high dimensional distribution of codons. It is expected that the signals are detectable by the score and procedure of the present embodiments, but not by single codon measures of codon usage bias.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] J. B. Plotkin and G. Kudla, "Synonymous but not the same: the causes and consequences of codon bias," Nat Rev Genet, vol. 12, pp. 32-42, January 2010.
[2] J. V. Chamary, et al., "Hearing silence: non-neutral evolution at synonymous sites in mammals," Nat Rev Genet, vol. 7, pp. 98-108, February 2006.
[3] Z. E. Sauna and C. Kimchi-Sarfaty, "Understanding the contribution of synonymous mutations to human disease," Nat Rev Genet, vol. 12, pp. 683-91, October 2013.
[4] L. Cartegni, et al., "Listening to silence and understanding nonsense: exonic mutations that affect splicing," Nat Rev Genet., vol. 3, pp. 285-98., April 2002.
[5] M. Kozak, "Point mutations define a sequence flanking the AUG initiator codon that modulates translation by eukaryotic ribosomes," Cell, vol. 44, pp. 283-292, 1986.
[6] H. Zur and T. Tuller, "New Universal Rules of Eukaryotic Translation Initiation Fidelity," PLoS Comput Biol, vol. 9, p. e1003136, 2013.
[7] V. Ramakrishnan, "Ribosome structure and the mechanism of translation," Cell., vol. 108, pp. 557-72., Feb. 22 2002.
[8] G. W. Li, et al., "The anti-Shine-Dalgarno sequence drives translational pausing and codon choice in bacteria," Nature, Mar. 28 2012.
[9] B. Alberts, et al., Molecular Biology of the Cell. New York, 2002.
[10] J. J. Forman and H. A. Coller, "The code within the code: microRNAs target coding regions," Cell Cycle., vol. 9, pp. 1533-41. Epub 2010 April 15., Apr. 15 2010.
[11] H. Zur and T. Tuller, "Strong association between mRNA folding strength and protein abundance in *S. cerevisiae*," EMBO Rep., 2012.
[12] D. J. Hogan, et al., "Diverse RNA-binding proteins interact with functionally related sets of RNAs, suggesting an extensive regulatory system," PLoS Biol., vol. 6, p. e255. doi: 10.1371/journal.pbio.0060255., Oct. 28 2008.
[13] A. B. Stergachis, et al., "Exonic transcription factor binding directs codon choice and affects protein evolution," Science., vol. 342, pp. 1367-72. doi: 10.1126/science.1243490, Dec. 13, 2013.
[14] W. Gu, et al., "A universal trend of reduced mRNA stability near the translation-initiation site in prokaryotes and eukaryotes," PLoS Comput Biol. 2010 vol. 6, pp. 1-8, 2010.
[15] T. Tuller, et al., "Composite Effects of Gene Determinants on the Translation Speed and Density of Ribosomes" Genome Biol, vol. 12, p. R110, 2011
[16] T. Tuller, et al., "An evolutionarily conserved mechanism for controlling the efficiency of protein translation," Cell, vol. 141, pp. 344-354, 2010.
[17] G. Kudla, et al., "Coding-sequence determinants of gene expression in *Escherichia coli*," Science, vol. 324, pp. 255-8, Apr. 10, 2009.
[18] G. Cannarozzi, et al., "A role for codon order in translation dynamics," Cell, vol. 141, pp. 355-67, Apr. 16, 2010.
[19] M. Schnall-Levin, et al., "Conserved microRNA targeting in *Drosophila* is as widespread in coding regions as in 3'UTRs," Proc Natl Acad Sci USA., vol. 107, pp. 15751-6. doi: 10.1073/pnas.1006172107. Epub 2010 Aug. 20, Sep. 7, 2010.
[20] J. Pevsner, Bioinformatics and Functional Genomics: John Wiley & Sons, 2013.
[21] P. M. Sharp and W. H. Li, "The codon Adaptation Index—a measure of directional synonymous codon usage bias, and its potential applications," Nucleic Acids Res, vol. 15, pp. 1281-95, Feb. 11, 1987.
[22] M. dos Reis, et al., "Solving the riddle of codon usage preferences: a test for translational selection," Nucleic Acids Res, vol. 32, pp. 5036-44, 2004.
[23] D. B. Goodman, et al., "Causes and effects of N-terminal codon bias in bacterial genes," Science., vol. 342, pp. 475-9. doi: 10.1126/science.1241934. Epub 2013 Sep. 26., Oct. 25, 2013.
[24] M. Wang, et al., "PaxDb, a Database of Protein Abundance Averages Across All Three Domains of Life," Molecular & cellular proteomics: MCP, vol. 11, pp. 492-500, August 2012.
[25] E. B. Vervoort, et al., "Optimizing heterologous expression in Dictyostelium: importance of 5' codon adaptation," Nucl. Acids Res., vol. 28, pp. 2069-2074, May 15, 2000.
[26] C. Gustafsson, et al., "Codon bias and heterologous protein expression," Trends Biotechnol, vol. 22, pp. 346-53, July 2004.
[27] J. Ziv and A. Lempel, "A universal algorithm for sequential data compression," Information Theory, IEEE Transactions on, vol. 23, pp. 337-343, 1977.
[28] I. Ulitsky, et al., "The average common substring approach to phylogenomic reconstruction," J Comput Biol, vol. 13, pp. 336-50, March 2006.
[29] Z. Bar-Joseph, et al., "Fast optimal leaf ordering for hierarchical clustering," Bioinformatics, vol. 17, pp. S22-29, Jun. 1, 2001.
[30] A. D. Wyner and A. J. Wyner, "An improved version of lempel-ziv algorithm," IEEE Tran. Inf. Theory., 1995.
[31] A. J. Wyner, "String matching theorems and applications to data compression and statistics," Ph.d. thesis, Stanford, 1993.
[32] M. Farach, et al., "On the entropy of DNA: Algorithms and measurements based on memory and rapid," in Symposium on Discrete Algorithms, 1994.
[33] U. Manber and G. Myers, "Suffix arrays: a new method for on-line string searches," First Annual ACM-SIAM Symposium on Discrete Algorithms, pp. 319-327, 1990.
[34] D. Gusfield, Algorithms on Strings, Trees and Sequences: Computer Science and Computational Biology: Cambridge University Press, 1999.
[35] M. Farach, "Optimal Suffix Tree Construction with Large Alphabets," in 38th IEEE Symposium on Foundations of Computer Science (FOCS '97), 1997, pp. 137-143.
[36] H. Theil, "Economic Forecasts and Policy, Vol. XV of Contributions to Economic Analysis," ed: North-Holland Pub. Co., Amsterdam, 1961.

What is claimed is:
1. A method of designing a polynucleotide sequence for expressing a polypeptide-of-interest (POI) in a host cell, the method comprising:

(a) generating a reference set of polynucleotide sequences;
(b) by a data processor, receiving said reference set of polynucleotide sequences of said host cell, and storing said reference set in a memory;
(c) by a data processor, generating for said reference set a suffix tree or a suffix array, and executing, in linear time, a procedure providing a concatenation of strings that encodes the POI, wherein said procedure employs an objective function directed to minimize coding regions which include genetic element sequences that do not appear in the host cell by searching over said suffix tree or suffix array to select strings of genetic elements, concatenating said strings of genetic elements to provide said concatenation, and storing said concatenation in a memory, wherein said suffix tree or suffix array allows finding a longest string of genetic elements encoding a portion of said POI starting at each position in the POI, and wherein said searching comprises: (i) weighing subsequences in said reference set so that longer subsequences are weighed with higher weights than shorter sequences, providing a selection criterion which is preferential for longer strings than for shorter strings, and (ii) weighing subsequences in said reference according to a selection criterion which is preferential for strings that are more frequent in said reference set than for strings that are less frequent in said reference set;
(d) by a data processor, embedding said concatenated strings in a transcript sequence encoding said POI to form a computer readable transcript sequence and storing said formed transcript sequence in a memory; and
(e) displaying said formed transcript sequence.

2. The method of claim 1, further comprising processing said strings by a dynamic programming method.

3. The method according to claim 2, wherein said processing comprises minimizing or reducing a number of said strings in said concatenation.

4. The method of claim 1, further comprising processing said plurality of strings by a dynamic programming method characterized by a recursion depth which is at most a length of said longest string of genetic elements.

5. The method of claim 1, wherein at least two of said strings are discontinuous.

6. The method of claim 1, wherein at least one of said strings is identified by analyzing in each codon or nucleotide position in said transcript sequence a longest string of nucleotides that starts in said position and is present in said reference set of polynucleotide sequences.

7. The method of claim 1, wherein said genetic elements are codon fragments.

8. The method of claim 1, wherein at least one of said strings comprise a coding sequence.

9. The method of claim 1, wherein at least one of said strings comprise a non-coding sequence.

10. The method of claim 1, wherein said genetic elements are codon pairs.

11. The method of claim 1, wherein said genetic elements are nucleotides.

12. The method of claim 1, wherein said reference set of polynucleotide sequences is selected from the group consisting of genomic DNA, RNA and ESTs.

13. The method of claim 1, further comprising embedding a biological molecule described by said concatenated strings in a biological molecule described by said transcript sequence.

14. The method of claim 1, wherein said selection criteria comprise: selecting a candidate subsequence that is more frequent among two candidate subsequences in said reference set when said two candidate subsequences are of equal lengths, and selecting a candidate subsequence that is longer among two candidate subsequences in said reference set when said two candidate subsequences appear in said reference set at the same frequency.

15. The method of claim 1, wherein at least one of said strings is at least 50 nucleotides long.

16. The method of claim 1, wherein said searching is executed in steps, and wherein at each of said steps a length of at least one of said strings is increased, by extending an end point of said at least one string or by searching for a string of increased length at a point following said end point.

17. The method of claim 1, wherein said the reference set comprises an entire genome of the host cell.

18. A method of designing a polynucleotide sequence for increasing expression of a polypeptide-of-interest (POI) in a cell, wherein said polypeptide of interest is endogenous to the cell, the method comprising:
(a) generating a reference set of polynucleotide sequences;
(b) by a data processor, receiving said reference set of polynucleotide sequences of said cell, and storing said reference set in a memory;
(c) by a data processor, generating for said reference set a suffix tree or a suffix array, and executing, in linear time, a procedure providing a concatenation of strings that encodes the POI, wherein said procedure employs an objective function directed to minimize coding regions which include genetic element sequences that do not appear in the host cell by searching over said suffix tree or suffix array to select strings of genetic elements, minimizing a number of said selected strings, concatenating said selected strings of genetic elements to provide said concatenation, and storing said concatenated strings in a memory, wherein said suffix tree or suffix array allows finding a longest string of genetic elements encoding a portion of said POI starting at each position in the POI, and wherein said at least one of said strings is not of a polynucleotide natively encoding the POI;
(d) embedding said concatenated strings in a transcript sequence encoding said POI to form a computer readable transcript sequence; and
(e) displaying said formed transcript sequence.

19. The method of claim 18, wherein said searching comprises weighing subsequences in said reference according to a selection criterion which is preferential for strings that are more frequent in said reference set than for strings that are less frequent in said reference set.

20. The method of claim 18, wherein said searching is executed in steps, and wherein at each of said steps a length of at least one of said strings is increased, by extending an end point of said at least one string or by searching for a string of increased length at a point following said end point.

21. The method of claim 18, wherein said the reference set comprises an entire genome of the host cell.

* * * * *